US007919101B2

(12) United States Patent
Jiang et al.

(10) Patent No.: US 7,919,101 B2
(45) Date of Patent: Apr. 5, 2011

(54) HIGHLY POTENT SYNERGISTIC COMBINATIONS OF HUMAN IMMUNODEFICIENCY VIRUS (HIV) FUSION INHIBITORS

(75) Inventors: Shibo Jiang, Fresh Meadows, NY (US); Chungen Pan, Guangzhou (CN)

(73) Assignee: New York Blood Center, New York, NY (US)

( * ) Notice: Subject to any disclaimer, the term of this patent is extended or adjusted under 35 U.S.C. 154(b) by 0 days.

(21) Appl. No.: 12/540,325

(22) Filed: Aug. 12, 2009

(65) Prior Publication Data
US 2010/0040631 A1    Feb. 18, 2010

Related U.S. Application Data

(60) Provisional application No. 61/088,571, filed on Aug. 13, 2008.

(51) Int. Cl.
*A61K 39/21* (2006.01)
(52) U.S. Cl. .................................. 424/188.1; 424/208.1
(58) Field of Classification Search .......................... None
See application file for complete search history.

(56) References Cited

U.S. PATENT DOCUMENTS
2004/0062767 A1* 4/2004 Olson et al. ................. 424/144.1
2007/0179278 A1   8/2007 Dwyer et al.

OTHER PUBLICATIONS

Gustchina, E., et al., 2007, A monoclonal Fab derived from a human nonimmune phage library reveals a new epitope on gp41 and neutralizes diverse human immunodeficiency virus type 1 strains, J. Virol. 81(23):12946-12953.*

Zwick, M. B., et al., 2005, Anti-human immunodeficiency virus type 1 (HIV-1) antibodies 2F5 and 4E10 require surprisingly few crucial residues in the membrane-proximal external region of glycoprotein gp41 to neutralize HIV-1, J. Virol. 79(2):1252-1261.*

Zwick, M. B., et al., 2001, Neutralization synergy of human immunodeficiency virus type 1 primary isolates by cocktails of broadly neutralizing antibodies, J. Virol. 75(24):12198-12208.*

Jiang, S., et al., 2004, N-substituted pyrrole derivatives as novel human immunodeficiency virus type 1entry inhibitors that interfere with the gp41 six-helix bundle formation and block virus fusion, Antimicrob. Agents Chemother. 48(11):4349-4359.*

Root, M. J., and D. H.Hamer, 2003, Targeting therapeutics to an exposed and conserved binding element of the HIV-1 fusion protein, Proc. Natl. Acad. Sci. USA 100(9):5016-5021.*

Pan, C., et al. 2009. Combinations of the first and next generations of human immunodeficiency virus (HIV) fusion inhibitors exhibit a highly potent synergistic effect against enfuvirtide-sensitive and -resistant HIV type 1 strains. J. Virol. 83(16):7862-7872.*

Tremblay, C. 2004. Effects of HIV-1 entry inhibitors in combination. Curr. Pharm. Des. 10:1861-1865.*

Buchacher et al. "Generation of human monoclonal antibodies against HIV-1 proteins; electrofusion and Epstein-Barr virus transformation for peripheral blood lymphocyte immortalization." AIDS Res Hum Retroviruses. vol. 10, No. 4, pp. 359-369, 1994.

(Continued)

*Primary Examiner* — Jeffrey S Parkin
(74) *Attorney, Agent, or Firm* — K&L Gates LLP; Louis C. Cullman; Michelle Glasky Bergman

(57) ABSTRACT

Provided herein are pharmaceutical compositions for the prophylactic and therapeutic treatment of HIV comprising combinations of HIV fusion/entry inhibitors that exhibit synergistic effect, including T-20 (enfuvirtide), T-1249, T-1144, C34, and sifuvirtide. Also disclosed are methods of treating HIV infection by administering such compositions.

10 Claims, 5 Drawing Sheets

```
IQN17    RMKQIEDKIEEIESKQKKIENEIARIKKLLQLTVWGIKQLQARIL    SEQ ID NO:44
N36             SGIVQQQNNLLRAIEAQQHLLQLTVWGIKQLQARIL    SEQ ID NO:40
N46      TLTVQARQLLSGIVQQQNNLLRAIEAQQHLLQLTVWGIKQLQARIL    SEQ ID NO:41
```

```
T-20              YTSLIHSLIEESQNQQEKNEQELLELDKWASLWNWF    SEQ ID NO:28
T-1249            WQEWEQKI-------TALLEQAQIQQEKNEYELQKLDKWASLWEWF    SEQ ID NO:34
T-1144      TTWEAWDRAIAEYAARIEALLRALQEQQEKNEAALREL         SEQ ID NO:10
C38         TTWMEWDREINNYTSLIHSLIEESQNQQEKNEQELLEL          SEQ ID NO:9
C34           WMEWDREINNYTSLIHSLIEESQNQQEKNEQELL            SEQ ID NO:5
Sifuvirtide   SWETWEREIENYTKQIYKILEESQEQQDRNEKDLLE          SEQ ID NO:7
CP32        QIWNNMTWMEWDREINNYTSLIHSLIEESQNQ                SEQ ID NO:16
CP32M       VEWNEMTWMEWEREIENYTKLIYKILEESQEQ                SEQ ID NO:17
```

OTHER PUBLICATIONS

Chan et al. "Core structure of gp41 from the HIV envelope glycoprotein." Cell, vol. 89, 263-273, 1997.

Chan et al. "Evidence that prominent cavity in the coiled coil of HIV type 1 gp41 is an attractive drug target." Proc. Natl. Acad. Scien. USA, col. 95, pp. 15613-15617, 1998.

Chan et al. "HIV entry and its inhibition." Cell, vol. 93, 681-684, 1998.

Chinnadurai et al. "Human Immunodeficiency Virus Type 1 Variants Resistant to First and Second Version Fusion Inhibitors and Cytopathic in Ex Vivo Human Lymphoid Tissue." Journal of Virology, p. 6563-6572, vol. 81, No. 12, 2007.

Debnath et al. "Structure-based identification of small molecule antiviral compounds targeted to the gp41 core structure of the human immunodeficiency virus type 1." J Med Chem. 42(17):3203-9, 1999.

Dwyer et al. "Design of helical, oligomeric HIV-1 fusion inhibitor peptides with potent activity against enfuvirtide-resistant virus." PNAS 12772-17222, vol. 104, No. 31, 2007.

Eckert et al. "Crystal structure of GCN4-pIQI, a trimeric coiled coil with buried polar residues." J. Mol. Biol. 284:859-865, 1998.

Eckert et al. "Inhibiting HIV-1 entry: discovery of D-peptide inhibitors that target the gp41 coiled-coil pocket." Cell. vol. 99, 103-115, 1999.

Eckert et al. "Design of potent inhibitors of HIV-1 entry from the gp41 N-peptide region." PNAS, vol. 98, No. 20, 11187-11192, 2001.

Eggink et al. "Selection of T1249-Resistant Human Immunodeficiency Virus Type 1 Variants." Journal of Virology, p. 6678-6688, vol. 82, No. 13, 2008.

Eron et al. "Short-term Safety and Antiretroviral Activity of T-1249, a Second-Generation Fusion Inhibitor of HIV." The Journal of Infectious Diseases, 189, 1075-1083, 2004.

He et al. "Indentification of a Critical Motif for the Human Immunodeficiency Virus Type 1 (HIV-1) gp41 Core Structure: Implications for Designing Novel Anti-HIV Fusion Inhibitors." Journal of Virology, p. 6349-6358, vol. 82, No. 13, 2008.

Hogg et al. "Antiviral effect of double and triple drug combinations amongst HIV-infected adults: lessons from the implementation of viral load-driven antiretroviral therapy." AIDS. 1998; 12:279-284.

Jiang et al. "HIV-1 inhibition by a peptide." Nature, vol. 365, 1993.

Jiang et al. "A Conformation-Specific Monoclonal Antibody Reacting with Fusion-Active gp41 from the Human Immunodeficiency Virus Type 1 Envelope Glycoprotein." Journal of Virology, p. 10213-10217, vol. 72, No. 12, 1998.

Jiang et al. "A screening assay for antiviral compounds targeted to the HIV-1 gp41 core structure using a conformation-specific monoclonal antibody." J. Virol. Methods 80, 1999, 85-96.

Jiang et al. "A convenient cell fusion assay for rapid screening for HIV entry inhibitors." Proc. SPIE. 2000; 3926:212-219.

Jiang et al. "N-Substituted Pyrrole Derivatives as Novel Human Immunodeficiency Virus Type 1 Entry Inhibitors that Interfere with the gp41 Six-Helix Bundle Formation and Block Virus Fusion." Antimicrobial Agents and Chemotherapy, p. 4349-4359, vol. 48, No. 11, 2004.

Kilby et al. "Potent suppression of HIV-1 replication in humans by T-20, a peptide inhibitor of gp41-mediated virus entry." Nature Med. 1998; 4:1302-1307.

Kilby et al. "The safety, plasma pharmacokinetics, and antiviral activity of subcutaneous enfuvirtide (T-20), a peptide inhibitor of gp41-mediated virus fusion, in HIV-infected adults." AIDS Res. Hum. Retroviruses. 2002; 18:685-693.

Kilby et al. "Novel therapies based on mechanisms of HIV-1 cell entry." N. Engl. J Med. 2003; 348:2228-2238.

Lalezari et al. "T-1249 retains potent antiretroviral activity in patients who had experienced virological failure while on an enfuvirtide-containing treatment regimen," J Infect. Dis. 2005; 191:1155-1163.

Lawless et al. "HIV-1 membrane fusion mechanism: structural studies of the interactions between biologically-active peptides from gp41." Biochemistry. Oct. 22, 1996;35(42):13697-708.

Liu et al. "Determination of the HIV-1 gp41 postfusion conformation modeled by synthetic peptides: applicable for identification of the HIV-1 fusion inhibitors." Peptide. 2003; 24:1303-1313.

Liu et al. "Different from the HIV fusion inhibitor C34, the anti-HIV drug Fuzeon (T-20) inhibits HIV-1 entry by targeting multiple sites in gp41 and gp120." J. Biol. Chem. 2005; 280:11259-11273.

Liu et al. "HIV gp41 C-terminal heptad repeat contains multifunctional domains: relation to mechanisms of action of anti-HIV peptides." J. Biol. Chem. 2007; 282:9612-9620.

Liu et al. "HIV entry inhibitors targeting gp41: from polypeptides to small-molecule compounds." Curr. Pharm. Des. 2007; 13:143-162.

Louis et al. "Design and properties of N(CCG)-gp41, a chimeric gp41 molecule with nanomolar HIV fusion inhibitory activity." J. Biol. Chem. 2001; 276:29485-29489.

Louis et al. "Covalent trimers of the internal N-terminal trimeric coiled-coil of gp41 and antibodies directed against them are potent inhibitors of HIV envelope-mediated cell fusion." J Biol. Chem. 2003; 278:20278-20285.

Lu et al. "A trimeric structural domain of the HIV-1 transmembrane glycoprotein." Nat. Struct. Biol. 1995; 2:1075-1082.

Menzo et al. "Genotype and Phenotype Patterns of Human Immunodeficiency Virus Type 1 Resistance to Enfuvirtide during Long-Term Treatment." Antimicrobial Agents and Chemotherapy, p. 3253-3259, vol. 48, No. 9, 2004.

Miller et al. "A human monoclonal antibody neutralizes diverse HIV-1 isolates by binding a critical gp41 epitope." PNAS, vol. 102, No. 41, 14759-14764, 2005.

Moore et al. "The entry of entry inhibitors: A fusion of science and medicine." PNAS, vol. 100, No. 19, 10598-10602, 2003.

Muster et al. "A Conserved Neutralizing Epitope on gp41 of Human Immunodeficiency Virus Type 1." Journal of Virology, p. 6642-6647, vol. 67, No. 11, 1993.

Neurath et al. "Anti-HIV-1 activity of cellulose acetate phthalate: Synergy with soluble CD4 and induction of "dead end" gp41 six-helix bundles." BMC Infectious Diseases, 2002, 2:6.

Ni et al. "Rational design of highly potent HIV-1 fusion inhibitory proteins: implication for developing antiviral therapeutics." Biochem. Biophys. Res. Commun. 2005; 332:831-836.

Pang et al. "Recombinant protein of heptad-repeat HR212, a stable fusion inhibitor with potent anti-HIV action in vitro." Virology. 2008; 377:80-87.

Root et al. "Protein design of an HIV-1 entry inhibitor." Science. 2001; 291:884-888.

Root et al. "Targeting therapeutics to an exposed an conserved binding element of the HIV-1 fusion protein." PNAS, 5016-5021, vol. 100, No. 9, 2003.

Root et al. "HIV-1 gp41 as a target for viral entry inhibition." Curr. Pharm. Des. 2004; 10:1805-1825.

Stiegler et al. "A potent cross-clade neutralizing human monoclonal antibody against a novel epitope on gp41 of human immunodeficiency virus type 1." AIDS Res Hum Retroviruses. Dec. 10, 2001;17(18):1757-65.

Suzuki et al. "An isoleucine zipper peptide forms a native-like triple stranded coiled coil in solution." Protein Engineering, vol. 11, No. 11, pp. 1051-1055, 1998.

Tremblay et al. "Strong in vitro synergy between the fusion inhibitor T-20 and the CXCR4 blocker AMD-3100." J Acquir Immune Defic Syndr. Oct. 1, 2000;25(2):99-102.

Wei et al. "Emergence of Resistant Human Immunodeficiency Virus Type 1 in Patients Receiving Fusion Inhibitor (T-20) Monotherapy." Antimicrobial Agents and Chemotherapy, p. 1896-1905, vol. 46, No. 6, 2002.

Weissenhorn et al. "Atomic Structure of the Ectodomain from HIV-1 gp41." Nature. 1997; 387:426-428.

Welch et al. "Potent D-peptide inhibitors of HIV-1 entry." PNAS, 16828-16833, vol. 104, No. 43, 2007.

Zhao et al. "XTT formazan widely used to detect cell viability inhibits HIV type 1 infection in vitro by targeting gp41." AIDS Res. Hum. Retroviruses. 2002; 18:989-997.

Zwick et al. Broadly Neutralizing Antibodies Targeted to the Membrane-Proximal External Region of Human Immunodeficiency Virus Type 1 Glycoprotein gp41. Journal of Virology, pp. 10892-10905, vol. 75, No. 22, 2001.

International Search Report, PCT/US2009/053619.

\* cited by examiner

Figure 1B

```
NHR  IQM17        RMKQIEDKIEEIESKQKKIENEIARIKKLLQLTVWGIKQLQARIL               SEQ ID NO:44
     N36                       SGIVQQQNNLLRAIEAQQHLLQLTVWGIKQLQARIL          SEQ ID NO:40
     N46(536-581) TLTVQARQLLSGIVQQQNNLLRAIEAQQHLLQLTVWGIKQLQARIL              SEQ ID NO:41
                      g    e   g    e   g    e   g    e   g    e
                 NH2-FP-MGAASMTLTVQARQLLSGIVQQQNNLLRAIEAQQHLLQLTVWGIKQLQARILAVERYLKDQ    SEQ ID NO:56
                      d    a   d    a   d    a   d    a   d    a                     ⌐
                                                                                      │
CHR              COOH-FWNWLSAWKDLELLEQENKEQQNSEELLSHLLSTYMNIERDMEMM-NH2               ⌐ SEQ ID NO:57

FWNWLSAWKDLELLEQENKEQQNSEELLSHILSTY                      T-20        SEQ ID NO:28
                 FWNWLSAWKDIKQLEYENKEQQIQAQELLAT------IERDMEMM            T-1249      SEQ ID NO:34
                       LERLAAENKEQQEQLARLLAEIRAAYEAIARDMAEMM               T-1144      SEQ ID NO:10
                              LLEQENKEQQNSEEILSHILSTYNNIERDMEMM            C38         SEQ ID NO:9
                              LLEQEMKEQQNSEELLSHILSTYMNIERDMEMM            C34         SEQ ID NO:5
                        ELLDKEMRDQQEQSEELIKYIQKTYNEIEREWTEWS               sifuvirtide SEQ ID NO:7
                          QNQSEELLSHILSTYNNIERDMEMMTMNMMIQ                 CP32        SEQ ID NO:16
                          QEQSEELIKYILKTYNEIEREMEMMTMEMMEV                 CP32M       SEQ ID NO:17
```

HIGHLY POTENT SYNERGISTIC COMBINATIONS OF HUMAN IMMUNODEFICIENCY VIRUS (HIV) FUSION INHIBITORS

CROSS-REFERENCE TO RELATED APPLICATIONS

The present application claims the benefit under 35 USC §119(e) to U.S. Provisional Patent Application 61/088,571 filed Aug. 13, 2008, the entire contents of which are incorporated by reference herein.

FIELD OF INVENTION

The present disclosure relates to the field of anti-viral agents. Specifically, the present disclosure relates to anti-viral agents comprising combinations of HIV fusion/entry inhibitors with different target sites in HIV gp41 or different mechanisms of action.

BACKGROUND OF THE INVENTION

Human immunodeficiency virus type 1 (HIV-1) envelope (Env) glycoprotein gp160 is proteolytically cleaved into the surface subunit gp120 that is responsible for virus binding to the receptors and the transmembrane fusion protein subunit gp41 that mediates virus fusion and entry. The gp41 molecule contains a cytoplasm domain (CT), a transmembrane domain (TM), and an extracellular domain (ectodomain) which consists of three major functional regions: fusion peptide (FP), N-terminal heptad repeat (NHR), and C-terminal heptad repeat (CHR). Both NHR and CHR regions are composed of 4-3 hydrophobic heptad repeat (HR) sequences which have a tendency to form coiled coil structure.

During HIV infection, gp120 binds to CD4 and a chemokine receptor (CCR5 or CXCR4) on the target cell to trigger gp41 structural rearrangement. This results in the formation of a stable gp41 six-helix bundle (6-HB) core structure, in which three NHR-helices associate to form the central trimeric coiled coil. Three C-helices pack obliquely in an antiparallel manner into the highly conserved hydrophobic grooves on the surface of the NHR-trimer. In each groove, there is a highly conserved hydrophobic deep pocket formed by the pocket-forming sequence (residues 565-581) in the NHR region. This pocket plays a critical role in viral fusion and maintaining the stability of the six-helix bundle. The formation of the six-helix bundle is believed to bring both the viral and target cell membranes into proximity, resulting in fusion between the virus and target cell membranes.

In the early 1990s, the first highly potent anti-HIV peptide, SJ-2176 (SEQ ID NO:3) was identified from the HIV-1 gp41 CHR region. Later, an analogous anti-HIV-1 peptide, T-20 (SEQ ID NO:29), was reported. In 2003, the US FDA approved the T-20 peptide (generic name: enfuvirtide; brand name Fuzeon®) as the first member of a new class of anti-HIV drugs—HIV fusion/entry inhibitors, which block HIV fusion with and entry into the target cell.

T-20 is effective as a salvage therapy for HIV/AIDS patients who have failed to respond to current antiretroviral therapeutics, including reverse transcriptase inhibitors (RTIs) and protease inhibitors (PIs). However, T-20 has several weaknesses. Firstly, it lacks oral bioavailability, resulting in an inconvenient dosage form and schedule, a significant barrier to patient acceptance and adherence. Secondly, its potency is not high. Thirdly, this peptidic drug can be easily degraded by proteolytic enzymes in the blood, leading to its short half-life in vivo (about 2 hours). Because of these problems, T-20 must be maintained in the blood of HIV/AIDS patients at a constant high concentration. Therefore, T-20 has to be administrated by injection twice a day at 90 mg/dose, resulting in painful injection-site reactions in most patients and high cost to the patients (>$20,000/year/patient). Furthermore, T-20 can easily induce drug resistance, resulting in increasing failure rates in T-20-treated patients. To overcome the above limitations of T-20, several approaches have been conducted, including modification of T-20 sequence or structure, designing of recombinant proteins interacting with the gp41 NHR or CHR regions, and identification of small molecule HIV-1 entry inhibitors targeting gp41.

HIV has an inherent tendency to mutate and may become resistant to any anti-HIV drugs. Patients with drug-resistant strains have an increasing risk of treatment failure with subsequent treatment regimen. Therefore, it is essential to develop new drugs with mechanisms of action or resistance profiles different from the current anti-HIV drugs. Application of existing drugs in combination therapies could improvevirologic response and reduce probability for viral mutations, or slow the development of drug resistance.

Clinical applications of antiretroviral drugs with different targets in combinations have shown significant synergism in inhibiting HIV-1 infection, reducing adverse effects and delaying the emergence of drug resistance. Therefore, a combination of two or more HIV fusion/entry inhibitors with different targets or different mechanisms of action may have the following advantages: 1) to maximize anti-HIV activity and to sustain effective anti-HIV concentrations for longer time because of synergistic effects; 2) to minimize potential toxic effects, reduce the amount and frequency of drug use, and decrease the cost to patient, due to dose reduction; and 3) to have complementary or cooperative anti-HIV activity.

BRIEF DESCRIPTION OF THE DRAWINGS

FIG. 3 depicts the interactions between combinations of an NHR-peptide, N46, and CHR-peptide(s) T1144, T-20, and T-1249 as determined by CD spectroscopy.

FIG. 4 depicts the synergistic effect of combinations of T-20 with T-1249 and/or T-1144 on the gp41 six-helix bundle formation as determined by ELISA.

SUMMARY OF THE INVENTION

Figure 1A:
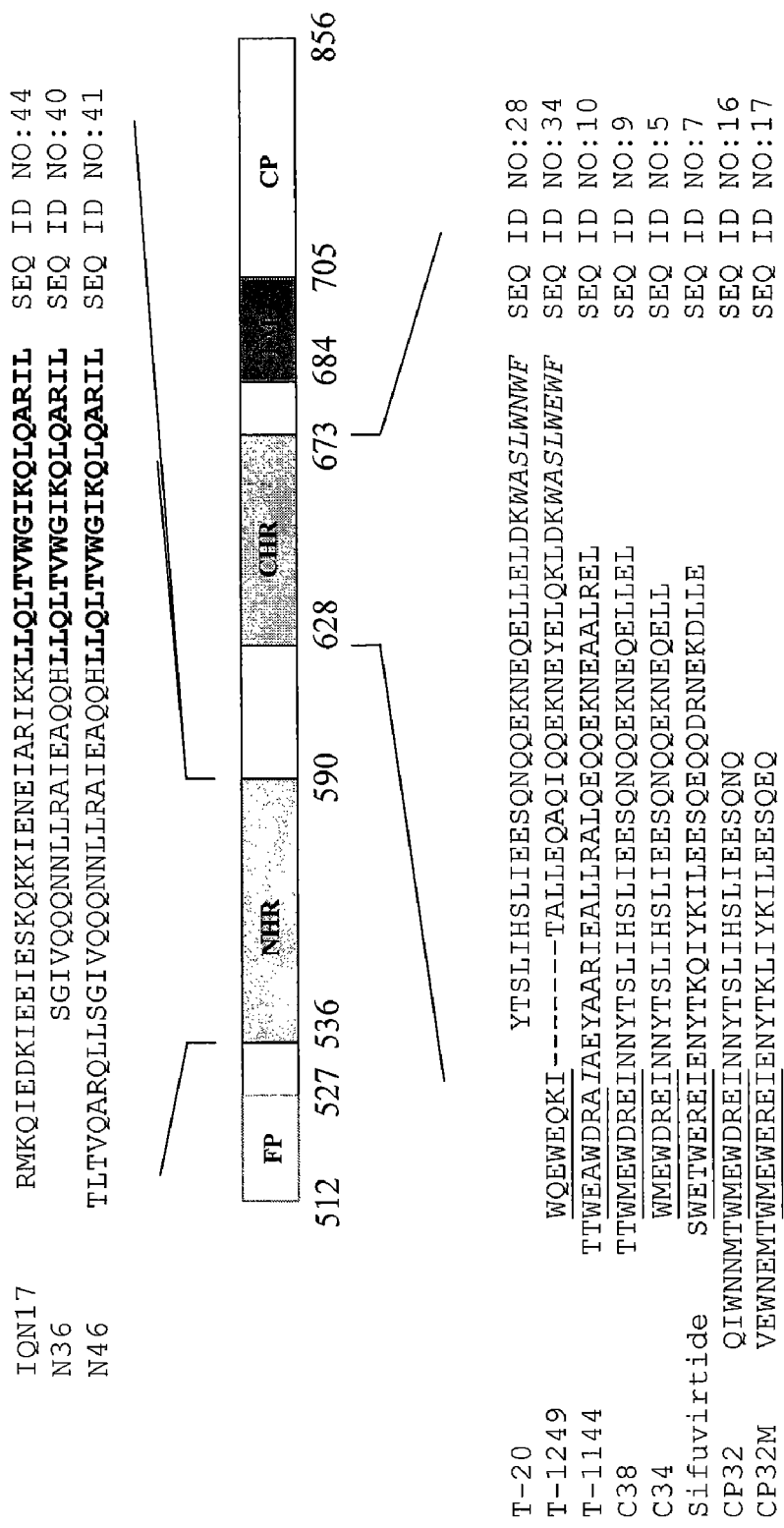
FIG. 1 depicts the sequences of the peptidic HIV fusion/entry inhibitors targeting gp41 (FIG. 1A) and the interactions between the N- and C-peptides (FIG. 1B).

Combinations of anti-HIV drugs targeting different sites on gp41 results in exceptionally potent synergistic anti-HIV activity. These findings suggest that administration of the HIV fusion/entry inhibitors targeting the different sites in gp41 or with different mechanisms of action may significantly increase the efficacy of the anti-HIV drugs, lead to a decrease in toxic effects, reduction of the amount and frequency of drug use, and consequently, these highly effective peptidic anti-HIV drugs will become more affordable to HIV/AIDS patients.

In one embodiment of the present disclosure a pharmaceutical composition is provided comprising a synergistic combination of two or more human immunodeficiency virus (HIV) fusion/entry inhibitors in amounts effective for treatment of HIV. In another embodiment, the HIV fusion/entry inhibitors target different regions in the HIV envelope glycoprotein transmembrane subunit of gp41. In another embodiment, the HIV fusion/entry inhibitors have different mechanisms of action.

In another embodiment, at least one of the HIV fusion/entry inhibitors is selected from the group consisting of an antibody targeting gp41, a peptide derived from gp41 or targeting gp41, a protein targeting gp41, a recombinant protein or polypeptide targeting gp41, and a small molecule organic compound targeting gp41.

In another embodiment, the antibodies targeting gp41 are monoclonal antibodies selected from the group consisting of 2F5, 4E10, Z13, and D5.

In yet another embodiment, the peptides targeting gp41 are selected from the group consisting of C28, C34, C35-EK, sifuvirtide, C36, C38, T-1144, T267227, T2635, C43, C46, CP32, CP32M, T-1249, PBD-4HR, PBD-4HRa, PBD-4HRb, PBD-4HRc, D10-p1-2K, D10-p5-2K, PIE7, CBD1, T-20, T-20-A, 4HR-LBD, 4HRa-LBD, 4HRb-LBD, 4HRc-LBD, N34, N36, N46, N51, DP-107, IQN17, ccIZN17, IZN28, IZN36, N34ccg, and VIRIP.

In yet another embodiment, the recombinant proteins or polypeptides targeting gp41 are selected from the group consisting of C52L, 5-Helix, N36ccg-N13, HR121, and HR212.

In yet another embodiment, the small molecule organic compounds are selected from the group consisting ADS-J1, NB-2, and NB-64.

In one embodiment, disclosed herein is a method of treating or preventing human immunodeficiency virus (HIV) infection comprising the steps of: administering a first HIV fusion/entry inhibitor; administering a second HIV fusion/entry inhibitor; and treating or preventing infection with HIV. In another embodiment, the method further comprises the step of administering a third HIV fusion/entry inhibitor. In another embodiment, the method further comprises the step of administering a fourth HIV fusion/entry inhibitor.

In another embodiment, the first and second HIV fusion/entry inhibitors are administered in a sequential manner, wherein each therapeutic agent is administered at a different time.

In another embodiment, the first and second HIV fusion/entry inhibitors are administered in a substantially simultaneous manner, by administering to the subject a dosage form comprising a single dosage unit comprising therein the desired doses of two or more HIV fusion/entry inhibitors or multiple dosage units, each dosage unit comprising a single HIV fusion/entry inhibitor.

In another embodiment, the administration is by a route selected from the group consisting of oral, topical, intravenous, intramuscular, and direct absorption through mucous membrane tissues. In another embodiment, each HIV fusion/entry inhibitor is individually administered by the same or by different routes. In yet another embodiment, the first HIV fusion/entry inhibitor is administered by intravenous injection and the second HIV fusion/entry inhibitor is administered orally.

DETAILED DESCRIPTION OF THE INVENTION

The phrase "combination therapy" (or "co-therapy") refers to the administration of two or more HIV fusion/entry inhibitors as part of a specific treatment or prevention regimen intended to provide a beneficial effect from the co-action of these therapeutic or prophylactic agents. The beneficial effect of the combination includes, but is not limited to, increased drug potency, deceased toxic effects, reduction in the amount and frequency of drug use, slowed development of drug-resistance, and improved pharmacokinetics or pharmacodynamics.

Administration of these therapeutic or prophylactic agents (hereinafter "compositions" or "agents") in combination typically is carried out over a defined time period. "Combination therapy" embraces administration of these HIV fusion/entry inhibitors in a sequential manner (i.e., each therapeutic or prophylactic agent is administered at a different time) or in a substantially simultaneous manner (e.g., administering to the subject a single dosage unit having a fixed ratio of each agent or in multiple, single dosage units for each agent). As used herein, the "dosage unit" refers to a physically discrete unit that contains a predetermined quantity of active ingredient calculated to produce a desired therapeutic or prophylactic effect. The unit dose or unit dosage may be in the form of tablet, capsule, inhalation capsule, suppository, oral or intravenous or topical solution or suspension, gel, or film, etc. For example, one embodiment of the present composition provides T-20 (the first generation HIV fusion inhibitor) and T-1249 (the second generation HIV fusion inhibitor) formulated as individual dosage units or a single, co-formulated dosage unit comprising the two compounds. In another example embodiment, the composition comprises T-20 and T1144 (the third generation HIV fusion inhibitor) as separate pharmaceutical composition dosage units that can be administered at the same or different time. As a further example embodiment, the composition comprises T-20, T1249 and T1144 as separate pharmaceutical composition dosage units that can be administered at the same or different time. Sequential or substantially simultaneous administration of each inhibitor can be effected by any appropriate route including, but not limited to, intravenous routes, intramuscular routes, oral routes, intravaginal routes, intrarectal routes, and direct absorption through mucous membrane tissues. Each HIV fusion/entry inhibitor can be administered by the same route or by different routes. For example, one component (e.g., T-20) may be administered by intravenous injection while the other component (e.g., NB-2) of the combination may be administered orally. The components may be administered in any therapeutically or prophylactically effective sequence.

The term "HIV fusion/entry" refers to a critical step of virus life cycle necessary for a virion or HIV-infected cell fusing with or entering into a target vesicle or cell.

The term "HIV fusion/entry inhibitor" refers to any agent that blocks HIV or HIV-infected cell fusion with or entry into a target vesicle or cell. HIV fusion/entry inhibitors include, but are not limited to peptides, small molecules and antibodies.

As used herein, the term "synergism" or "synergistic," when referring to synergism between drugs, means that the drugs interact in ways that enhance or magnify one or more effects, or side effects, of those drugs. This is sometimes exploited in combination preparations. The combination causes a greater effect than simply the sum of the individual effects of each drug if they were used separately.

HIV fusion/entry inhibitor antibodies include, but are not limited to, 2F5 (anti-HIV-1 gp41 monoclonal antibody; Buchacher A et al. AIDS Res. Human Retroviruses 10:359-369, 1994), 4E10 (anti-HIV-1 gp41 monoclonal antibody; Stiegler G et al. AIDS Res. Human Retroviruses 17:1757-1765, 2001), Z13 (IgG1 anti-HIV-1 gp41 monoclonal antibody; Zwick M B et al. J. Virol. 75:10892-905, 2001), and D5

(human anti-HIV-1 gp41 monoclonal antibody; Miller M D et al. Proc. Natl. Acad. Sci. 102:14759-14764, 2005).

SJ-2176 (SEQ ID NO:3), C34 (SEQ ID NO:5), C36 (SEQ ID NO:8), and C38 (SEQ ID NO:9), and other CHR-peptides containing the pocket-binding domain are believed to inhibits HIV fusion/entry by interacting with the HIV gp41 NHR and pocket regions, and blocking the formation of the six-helix bundle core of gp41. T-20, which contains the NHR- and lipid-binding domains but lacks the pocket-binding domain, may inhibit HIV fusion/entry by interacting with the HIV gp41 NHR region and lipid membrane.

T-1249 (SEQ ID NO:34), a second generation HIV fusion/entry inhibitor, is a 39-mer hybrid polypeptide consisting of a core peptide linked by a pocket-binding domain and a lipid-binding domain at the N- and C-termini, respectively. Therefore, it may inhibit HIV fusion/entry by interacting with the HIV gp41 NHR and pocket regions as well as the lipid membrane. T-1249 has a longer half-life than T-20 in primates and different resistant profiles. Clinical studies have shown that T-1249 exhibits greater anti-HIV-1 potency than T-20 and is active against some of T-20-resistant HIV-1 variants), indicating that T-1249 targets a different region from that of T-20 within the gp41 NHR.

T-1144 (SEQ ID NO:10), a 38-mer peptide, has been developed as the third generation HIV fusion/entry inhibitor. Like C38, T-1144 also contains the NHR- and pocket-binding domains, and is expected to inhibit HIV fusion/entry by interacting with the HIV gp41 NHR and pocket regions, and blocking the formation of the six-helix bundle core of gp41. T-1144 was designed by modifying the amino acid sequence of C38 to increase the helicity and six-helix bundle stability. It is thousands fold more active than T-20 against viruses that are resistant to T-20. The pharmacokinetic properties of T-1144 were improved up to 100-fold. The potent antiviral activity against resistant viruses, the difficulty in generating resistant virus, and the extended half-life in vivo make T-1144 attractive for further development.

Sifuvirtide (SEQ ID NO:7), a 36-mer peptide, was designed by modification of the CHR-peptide C36 based on three-dimensional (3D) structural information of HIV-1 gp41 and computer modeling analysis to favor its stability, pharmacokinetics, and antiviral potency. Like C36, sifuvirtide also contains the NHR- and pocket-binding domains. It may inhibit HIV fusion/entry by interacting with the HIV gp41 NHR and pocket regions, and blocking the formation of the six-helix bundle core of gp41. Sifuvirtide inhibited HIV-1-mediated cell-cell fusion in dose-dependent manner and exhibited higher potency than T-20 against infections by a wide range of primary and laboratory-adapted HIV-1 isolates from multiple genotypes with R5 or X4 phenotypes. Sifuvirtide was highly effective against T-20-resistant strains. Phase Ia clinical studies of sifuvirtide in healthy individuals demonstrated good safety, tolerability and pharmacokinetic profiles. Pharmacokinetic studies of single and multiple administration of sifuvirtide showed that its decay half-life was 20.0±8.6 hr and 26.0±7.9 hr, respectively.

CP32 (SEQ ID NO:16) is a 32-mer peptide containing the NHR- and pocket-binding domains and a motif (QIWNNMT, SEQ ID NO:54), which is located at the upstream region of the CHR and immediately adjacent to the pocket-binding domain and is highly important for the stabilization of the gp41 core structure. CP32 can interact with NHR-peptide T-21, a counterpart peptide derived from the NHR, to form a typical six-helix bundle structure with higher thermostability (Tm=81° C.) than that formed by the peptides N36 and C34 (Tm=65° C.). CP32 could efficiently bind to the gp41 pocket region and block six-helix bundle formation in a dose-dependent manner. Significantly, CP32 has potent inhibitory activity against HIV-1-mediated cell-cell fusion and infection by primary HIV-1 isolates. Unlike T-20 and C34 however, CP32 does not contain the GIV-binding sequence. Therefore, the mutations of GIV motif may have little or no effect at all on the interaction of CP32 with the viral gp41 NHR region, and consequently CP32 is very effective against HIV-1 strains resistant to T-20 and C34.

CP32M (SEQ ID NO:17) is an analogous peptide of CP32 with improved thermostability (Tm=94° C.) and enhanced anti-HIV-1 activity, especially against HIV-1 strains resistant to T-20, C34 and T-1249.

5-Helix is composed of three N-peptides (N40, residues 543-582) and two C-peptides (C-38, residues 625-662), connected by -GGSGG-linkers. Under physiological conditions, 5-Helix is well folded, soluble and extremely stable with a typical α-helical conformation. Because 5-Helix contains five of the six helices and has one groove exposed on the surface, it can attract one of the gp41 C-helices to fill in the gap and prevent the formation of fusion-active six-stranded gp41 core, thus blocking HIV-mediated membrane fusion. The high potency of 5-Helix against HIV infection (nanomolar $EC_{50}$) suggests that this polypeptide may be developed as a new anti-HIV therapeutic for preventing HIV entry. Furthermore, an exotoxin protein from a Pseudomonas strain was conjugated to the 5-Helix. This chimeric fusion protein can specifically bind to the CHR region of the viral gp41 expressed on the HIV-1-infected cells. Therefore, this recombinant toxin, like a "biological missile", can specifically attack the HIV-1-infected cells by killing these cells with its toxin component or block fusion of the HIV-1-infected cells with uninfected cells with its 5-Helix.

N35ccg-N13 (SEQ ID NO:49) and N34ccg (SEQ ID NO:48), are NHR-peptides, in which Leu576, Gln577 and Ala578 were replaced with Cys, Cys and Gly, respectively. These two NHR-peptides can form helical trimers which are stabilized by three intermolecular disulfide bonds. N35ccg-N13 and N34ccg can interact with the gp41 CHR domain and inhibit the HIV-induced cell-cell fusion with $EC_{50}$ values of 15 and 95 nM, respectively.

HR121 (SEQ ID NO:50) and HR212 (SEQ ID NO:22) are recombinant proteins with potent anti-HIV-1 activity. HR121 contains two molecules of N-peptide (N34) derived from the NHR (or HR1) region and one molecule of C-peptide (C34) derived from the gp41 CHR (or HR2) region connected by linkers in the order of HR1-HR2-HR1. Similarly, HR212 consists of two molecules of C-peptide (C34) and one molecule of N-peptide (N34) linked in the order of HR2-HR1-HR2. The rational for this design is that three heptad repeats (two N-peptides and one C-peptide, or one C-peptide and two N-peptides) are linked by flexible linkers so that N- and C-peptides in each protein can associate to form a hairpin structure. As a consequence, three molecules can form a stable six-helix bundle with three free N- or C-peptides exposed, which may bind to the counterpart regions in the viral gp41, thereby blocking gp41-mediated membrane fusion. Both HR121 and HR212 can be abundantly expressed and easily purified, exhibiting a stable α-helical character as shown in CD spectroscopy. The recombinant proteins HR121 and HR212 had potent inhibitory activity on HIV-1 Env-mediated cell-cell fusion with $EC_{50}$ values in low nanomolar range, being comparable to the potency of C-peptides, T-20 and C34 and much better than the N-peptides, T-21 and N36. These data suggest that HR121 and HR212 can be potentially developed as therapeutic agents, in a manner analogous to synthetic C-peptides, but may be much less expensive than the synthetic peptides since these recombinant protein can be easily expressed and purified in large scale.

D10-p1-2K (SEQ ID NO:23), D10-p5-2K (SEQ ID NO:24) and PIE7 (SEQ ID NO:25) are short peptides consisting of all D-amino acids which are resistant to proteolytic enzymes. These peptides can specifically bind to the gp41 hydrophobic pocket presented on the NHR-trimer modeled by IQN17, which was confirmed by X-ray crystallography and nuclear magnetic resonance (NMR). D10-p5-2K and PIE7 can inhibit HIV-1 infection with $EC_{50}$ in low micromolar range. These anti-HIV D-peptides are expected to be resistant to proteolytic degradation.

ADS-J1 is the first small molecule HIV fusion/entry inhibitor identified with a series of high throughput screening (HTS) assays, including the virtual screening method based on computer modeling to screen for compounds with potential to dock into the deep hydrophobic pocket on the gp41 N-helix trimer and ELISA and cell fusion assays for compounds with inhibitory activity against gp41 six-helix bundle formation and HIV-1-mediated membrane fusion, respectively. ADS-J1 inhibited HIV replication, HIV-1 mediated cell-cell fusion and the gp41 6-HB formation with $EC_{50}$ is in low μM range (Debnath A K et al. J Med Chem 42:3203-3209, 1999).

NB-2 and NB-64, the N-substituted pyrroles, were identified from a chemical library consisting of 33,040 "drug-like" compounds from ChemBridge Corp using HTS assays (Jiang S et al. Antimicrob Agents Chemother 48:4349-4359, 2004). NB-2 and NB-64 may bind to the gp41 pocket and block the 6-HB formation. These compounds inhibited infection by both laboratory-adapted and primary HIV-1 strains with distinct genotypes (clades A to G and group O) and phenotypes (R5, X4 and R5X4) at low micromolar levels. NB-2 and NB-64 effectively inhibited HIV-1 Env-mediated cell-cell fusion and blocked the formation of the fusion-active gp41 6-HB as demonstrated by several assay systems, such as ELISA, FN-PAGE and CD analysis. Computer-aided molecular docking analysis has shown that both compounds fit inside the hydrophobic pocket and their COOH group interacts with a positively charged residue (K574) around the pocket to form a salt bridge, thereby blocking the formation of the 6-HB and ultimately inhibiting HIV-1 mediated membrane fusion.

TABLE 1

Sequences of the peptidic HIV fusion/entry inhibitors targeting gp41

| Molecule | SEQ ID NO | Sequence |
|---|---|---|
| Peptidic fusion/entry inhibitors targeting gp41 NHR and/or pocket region | | |
| PBD | 1 | WMEWDREI |
| HBD | 2 | NNYTSLIHSLIEESQNQQEKNEQELLELDK |
| SJ-2176 | 3 | EWDREINNYTSLIHSLIEESQNQQEKNEQE |
| C28 | 4 | WMEWDREINNYTSLIHSLIEESQNQQEK |
| C34 | 5 | WMEWDREINNYTSLIHSLIEESQNQQEKNEQELL |
| C35-EK | 6 | WEEWDKKIEEYTKKIEELIKKSEEQQKKNEEELKK |
| Sifuvirtide | 7 | SWETWEREIENYTKQIYKILEESQEQQDRNEKDLLE |
| C36 | 8 | WMEWDREINNYTSLIHSLIEESQNQQEKNEQELLEL |
| C38 | 9 | TTWMEWDREINNYTSLIHSLIEESQNQQEKNEQELLEL |
| T-1144 | 10 | TTWEAWDRAIAEYAARIEALLRALQEQQEKNEAALREL |
| T267227 | 11 | TTWEAWDRAIAEYAARIEALIRAAQEQQEKLEAALREL |
| T2635 | 12 | TTWEAWDRAIAEYAARIEALIRAAQEQQEKNEAALREL |
| C43 | 13 | NHTTWMEWDREINNYTSLIHSLIEESQNQQEKNEQELLELDKW |
| C46 | 14 | WMEWDREINNYTSLIHSLIEESQNQQEKNEQELLELDKWASLWNWF |
| C52L | 15 | NHTTWMEWDREINNYTSLIHSLIEESQNQQEKNEQELLELDKWASLWNWFNIKIL |
| CP32 | 16 | QIWNNMTWMEWDREINNYTSLIHSLIEESQNQ |
| CP32M | 17 | VEWNEMTWMEWEREIENYTKLIYKILEESQEQ |
| PBD-4HR | 18 | WMEWDREIEEYTKKIEEYTKKIEEYTKKIEEYTKKI |
| PBD-4HRa | 19 | WMEWDREIEEYTKKIEEYTKKIEEYTKKIEEYTKKI |
| PBD-4HRb | 20 | WMEWDREIEELAKKAEELAKKAEELAKKAEELAKKA |
| PBD-4HRc | 21 | WMEWDREIEEAAKKLEEAAKKLEEAAKKLEEAAKKL |
| HR212 | 22 | WMEWDREINNYTSLIHSLIEESQNQQEKNEQELLGGSGGSGIVQQQNNLLRAIEAQQHLLQLTVWGIKQLQARILGSSGGWMEWEREINNYTSLIHSLIEESQNQQEKNEQELL |
| D10-p1-2K | 23 | KKGACEARHREWAWLCAA |
| D10-p5-2K | 24 | KGACELLGWEWAWLCAA |
| PIE7 | 25 | KGACDYPEWQWLCAA |
| CBD1 | 26 | SLEQIWNNMTWMQWDK |
| Peptidic fusion/entry inhibitors targeting gp41 NHR and lipid membrane | | |
| TRD | 27 | WASLWNWF |
| T-20 | 28 | YTSLIHSLIEESQNQQEKNEQELLELDKWASLWNWF |
| T-20-A | 29 | HSLIEESQNQQEKNEQELLELDKWASLWNWFNITNW |
| 4HR-LBD | 30 | EEYTKKIEEYTKKIEEYTKKIEEYTKKIWASLWNWF |
| 4HRa-LBD | 31 | EELAKKAEELAKKAEELAKKAEELAKKAWASLWNWF |
| 4HRb-LBD | 32 | EEAAKKLEEAAKKLEEAAKKLEEAAKKLWAS |

TABLE 1-continued

Sequences of the peptidic HIV fusion/entry inhibitors targeting gp41

| Molecule | SEQ ID NO | Sequence |
|---|---|---|
| 4HRc-LBD | 33 | EALAKAAEALAKAAEALAKAAEALAKAAWAS LWNWF |

Peptidic fusion/entry inhibitors targeting gp41 pocket and NHR region and lipid membrane

| Molecule | SEQ ID NO | Sequence |
|---|---|---|
| T-1249 | 34 | WQEWEQKITALLEQAQIQQEKNEYELQKLDK WASLWEWF |
| PBD-3HR-LBD | 35 | WMEWDREIEEYTKKIEEYTKKIEEYTKKIWA SLWNWF |
| PBD-3HRa-LBD | 36 | WMEWDREIEELAKKAEELAKKAEELAKKAWA SLWNWF |
| PBD-3HRb-LBD | 37 | WMEWDREIEEAAKKLEEAAKKLEEAAKKLWA SLWNWF |
| PBD-3HRc-LBD | 38 | WMEWDREIEALAKAAEALAKAAEALAKAAWA SLWNWF |

Peptidic fusion/entry inhibitors targeting gp41 CHR region

| Molecule | SEQ ID NO | Sequence |
|---|---|---|
| N34 | 39 | SGIVQQQNNLLRAIEAQQHLLQLTVWGIKQL QAR |
| N36 | 40 | SGIVQQQNNLLRAIEAQQHLLQLTVWGIKQL QARIL |
| N46 | 41 | TLTVQARQLLSGIVQQQNNLLRAIEAQQHLL QLTVWGIKQLQARIL |
| N51 | 42 | QARQLLSGIVQQQNNLLRAIEAQQHLLQLTV WGIKQLQARILAVERYLKQQ |
| DP-107 | 43 | NNLLRAIEAQQHLLQLTVWGIKQLQARILAV ERYLKDQ |
| IQN17 | 44 | RMKQIEDKIEEIESKQKKIENEIARIKKLLQ LTVWGIKQLQARIL |
| ccIZN17 | 45 | CDGGIKKEIEAIKKEQEAIKKKIEAIEKLLQ LTVWGIKQLQARIL |
| IZN28 | 46 | IKKEIEAIKKEQEAIKKKIEAIEKEIEAQQH LLQLTVWGIKQLQARILAVERY |
| IZN36 | 47 | IKKEIEAIKKEQEAIKKKIEAIEKEISGIVQ QQNNLLRAIEAQQHLLQLTVWGIKQLQARIL |
| N34ccg | 48 | SGIVQQQNNLLRAIEAQQHLLQLTVWGIKQC CGR |
| N35ccg-N13 | 49 | SGIVQQQNNLLRAIEAQQHLLQLTVWGIKQC CGRISGIVQQQNNLLRA |
| HR121 | 50 | SGIVQQQNNLLRAIEAQQHLLQLTVWGIKQL QARILGSSGGWMEWQREINNYTSLIHSLIEE SQNQQEKNEQELLGGSGGSGIVQQQNNLLRA IEAQQHLLQLTVWGIKQLQARIL |
| 5-helix | 51 | QLLSGIVQQQNNLLRAIEAQQHLLQLTVWGI KQLQARILAGGSGGHTTWMEWDREINNYTSL IHSLIEESQNQQEKNEQELLEGSSGGQLLSG IVQQQNNLLRAIEAQQHLLQLTVWGIKQLQA RILAGGSGGHTTWMEWDREINNYTSLIHSLI EESQNQQEKNEQELLEGSSGGQLLSGIVQQQ NNLLRAIEAQQHLLQLTVWGIKQLQARILA |

Peptidic fusion/entry inhibitors targeting gp41 fusion peptide

| Molecule | SEQ ID NO | Sequence |
|---|---|---|
| VIRIP | 52 | LEAIPMSIPPEVKFNKPFVF |
| VIR576 | 53 | LEAIPCSIPPEFLFGKPFVF |

The term "therapeutic effect" refers to one or more of the following: 1) inhibition of fusion of a virion or HIV-infected cell with a target cell; 2) inhibition of HIV replication; 3) reduction in the number of infected cells; 4) reduction in the concentration of virions present in serum; 5) increasing T-cell count; 6) relieving or reducing to some extent one or more of the symptoms associated with HIV; and 7) relieving or reducing the side effects associated with the administration of other antiretroviral agents. "Therapeutically effective amount" is intended to qualify the amount required to achieve a therapeutic effect.

The term "prophylactic effect" refers to prevention of a virion or HIV-infected cell to enter into and replicate in a target cell.

"Prophylactically effective amount" is intended to qualify the amount required to achieve a preventive effect The terms "$EC_{50}$" and "$EC_{90}$" refer to the drug concentration that results in a 50% and 90% reduction, respectively, in virus replication or virus-mediated cell fusion.

As used herein, the term "inhibit," "inhibition," "inhibitory" and "inhibitory activity" refers to slowing, decreasing, interrupting, arresting or suppressing HIV assembly, maturation and replication activity so as to enable prolonging the survivability of the patient. In some embodiments, the claimed composition may suppress 90%, 80%, 70%, 60%, 50%, 40%, 30%, 20%, or 10% of the retroviral activity. $IC_{50}$ is well understood by a person of skill in the art to be the accepted measure of the effectiveness of inhibition. The measurement indicates how much of a particular substance is necessary to decrease or inhibit a particular activity by 50%.

As used herein "prodrug" refers to a compound which is converted to a therapeutically active compound after administration, and the term should be interpreted as broadly herein as is generally understood in the art. While not intending to limit the scope of the present description, conversion may occur by hydrolysis of an ester group or some other biologically labile group. Generally, but not necessarily, a prodrug is inactive or less active than the therapeutically active compound to which it is converted. Ester prodrugs of the compounds disclosed herein are contemplated.

The term "therapeutically effective amount" or "pharmaceutically effective amount" means an amount of composition sufficient to, when administered to a subject suffering from or susceptible to HIV infection and/or one or more associated diseases, disorders or conditions, treat HIV infection and/or associated disease(s), disorder(s) or condition(s).

The terms "treat," "treatment" or "treating," as used herein, refer to partially or completely alleviating, inhibiting, preventing, curing, delaying the onset of, reducing incidence of, ameliorating and/or relieving one or more symptoms or features of a particular disease, disorder or condition (e.g., HIV infection).

The pharmaceutical compositions herein disclosed comprise a therapeutically effective amount of HIV-1 fusion/entry inhibitor formulated for administration to a subject at risk of infection with HIV or to a patient suffering from or susceptible to an HIV infection and/or an associated disease, disorder or condition. Some of the disclosed compositions include at least one pharmaceutically acceptable excipient and may optionally include at least one additional therapeutically active agent.

The disclosed fusion/entry inhibitors may be administered in free form or, where appropriate, as a pharmaceutically acceptable derivative thereof. In some embodiments, the disclosed compounds are administered in a salt form; in other embodiments, the compounds are administered in an ester or prodrug form.

Appropriate excipients for use in the present pharmaceutical compositions may include, for example, one or more carriers, binders, fillers, vehicles, disintegrants, surfactants, dispersion or suspension aids, thickening or emulsifying agents, isotonic agents, preservatives, lubricants, and the like or combinations thereof, as suited to a particular dosage from desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. This document is incorporated herein by reference in its entirety.

The disclosed compositions may be formulated for any desirable route of delivery including, but not limited to, parenteral, intravenous, intradermal, subcutaneous, oral, topical, inhalative, transdermal, topical, transmucosal, rectal, interacisternal, intravaginal, intraperitoneal, bucal and intraocular.

In certain aspects, parenteral, intradermal or subcutaneous formulations may be sterile injectable aqueous or oleaginous suspensions. Acceptable vehicles, solutions, suspensions and solvents may include, but are not limited to, water or other sterile diluent; saline; Ringer's solution; sodium chloride; fixed oils such as mono- or diglycerides; fatty acids such as oleic acid; polyethylene glycols; glycerine; propylene glycol or other synthetic solvents; antibacterial agents such as benzyl alcohol; antioxidants such as ascorbic acid; chelating agents such as ethylenediaminetetraacetic acid; buffers such as acetates, citrates or phosphates; and agents for the adjustment of tonicity such as sodium chloride or dextrose.

Solutions or suspensions used for parenteral, intradermal, or subcutaneous application may include one or more of the following components: a sterile diluent such as water for injection, saline solution, fixed oils, polyethylene glycols, glycerine; propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose. The pH can be adjusted with acids or bases, such as hydrochloric acid or sodium hydroxide. The parenteral preparation may be enclosed in ampoules, disposable syringes or multiple dose vials made of glass or plastic.

Pharmaceutical compositions suitable for injectable use may include sterile aqueous solutions or dispersions and sterile powders for the extemporaneous preparation of sterile injectable solutions or dispersion. For intravenous administration, suitable carriers include, but are not limited to, saline, bacteriostatic water, CREMOPHOR EL® (BASF, Parsippany, N.J.) or phosphate buffered saline (PBS). The solvent or dispersion medium may contain, for example, water, ethanol, polyol (for example, glycerol, propylene glycol, and liquid polyetheylene glycol, and the like), and suitable mixtures thereof. Proper fluidity can be maintained, for example, by the use of a coating such as lecithin, by the maintenance of the requited particle size in the case of dispersion and by the use of surfactants. Preventing growth of microorganisms can be achieved by various antibacterial and antifungal agents, for example, parabens, chlorobutanol, phenol, ascorbic acid, thimerosal, and the like. The composition may also include isotonic agents such as, for example, sugars; polyalcohols such as manitol; sorbitol; or sodium chloride. Prolonged absorption of injectable compositions can be enhanced by addition of an agent which delays absorption, such as, for example, aluminum monostearate or gelatin.

Oral compositions may include an inert diluent or an edible carrier. They may be enclosed in gelatin capsules or compressed into tablets. Tablets, pills, capsules, troches and the like can contain any of the following ingredients, or compounds of a similar nature: a binder such as microcrystalline cellulose, gum tragacanth or gelatin; an excipient such as starch or lactose; a disintegrating agent such as alginic acid, Primogel, or corn starch; a lubricant such as magnesium stearate or sterites; a glidant such as colloidal silicon dioxide; a sweetening agent such as sucrose or saccharin; or a flavoring agent such as peppermint, methyl salicylate, or orange flavoring.

Systemic administration may be by transmucosal or transdermal means. For transmucosal or transdermal administration, penetrants may be used. Such penetrants are generally known in the art, and include, for example, detergents, bile salts, and fusidic acid derivatives. Transdermal administration may include a bioactive agent and may be formulated into ointments, salves, gels, or creams as generally known in the art. Transmucosal administration may be accomplished through the use of nasal sprays or suppositories.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

For administration topically to external tissues e.g., mouth, skin, vagina, rectum, etc., the formulations may applied as a topical ointment, cream or gel containing the active ingredient(s) in an amount of, for example, 0.075 to 20% w/w (including active ingredient(s) in a range between 0.1% and 20% in increments of 0.1% w/w such as 0.6% w/w, 0.7% w/w, etc.), preferably 0.2 to 15% w/w and most preferably 0.5 to 10% w/w. When formulated in an ointment, the HIV-1 fusion/entry inhibitors may be employed with either a paraffinic or a water-miscible ointment base. Alternatively, the active ingredients may be formulated in a cream with an oil-in-water cream base.

If desired, the aqueous phase of the cream base may include, for example, at least 30% w/w of a polyhydric alcohol, i.e. an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the HIV-1 fusion/entry inhibitors through the skin or other affected areas. Examples of such dermal penetration enhancers include dimethyl sulphoxide and related analogs.

The oily phase of the emulsions may be constituted from known ingredients in a known manner. While the phase may comprise merely an emulsifier (otherwise known as an emulgent), it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations.

Emulgents and emulsion stabilizers suitable for use in the formulation include TWEEN® 60, SPAN® 80, cetostearyl alcohol, benzyl alcohol, myristyl alcohol, glyceryl monostearate and sodium lauryl sulfate.

The choice of suitable oils or fats for the formulation is based on achieving the desired cosmetic properties. The cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils are used.

Formulations suitable for vaginal administration may be presented as pessaries, tampons, creams, gels, pastes, foams or spray formulations containing in addition to the HIV-1 fusion/entry inhibitors such carriers as are known in the art to be appropriate The disclosed HIV-1 fusion/entry inhibitors are useful in treating HIV-1 infections and/or associated diseases, disorders and conditions. The pharmaceutical compositions comprising at least one fusion/entry inhibitor may be administered to individuals suffering from or susceptible to HIV-1 infection.

The pharmaceutical compositions comprising the fusion/entry inhibitors may be administered in a therapeutically effective amount, according to an appropriate dosing regiment. As understood by a skilled artisan, an exact amount required may vary from subject to subject, depending on a subject's species, age and general condition, the severity of the infection, the particular agent(s) and the mode of administration. In some embodiments, about 0.001 mg/kg to about 50 mg/kg, of the pharmaceutical composition based on the subject's body weight is administered, one or more times a day, to obtain the desired therapeutic effect. In other embodiments, about 1 mg/kg to about 25 mg/kg, of the pharmaceutical composition based on the subject's body weight is administered, one or more times a day, to obtain the desired therapeutic effect.

A total daily dosage of the compounds and pharmaceutical compositions can be determined by the attending physician within the scope of sound medical judgment. A specific therapeutically effective dose level for any particular patient or subject will depend upon a variety of factors including the disorder being treated and the severity of the disorder; the activity of the specific compound employed; the specific composition employed; the age, body weight, general health, sex and diet of the patient or subject; the time of administration, route of administration, and rate of excretion of the specific compound employed; the duration of the treatment; drugs used in combination or coincidental with the specific compound employed, and other factors well known in the medical arts.

The disclosed compounds and compositions may also be employed in combination therapies. That is, the compounds and pharmaceutically acceptable compositions presently disclosed can be administered concurrently with, prior to, or subsequent to, at least one other desired composition, therapeutic, treatment or medical procedure. A particular combination of therapies administered can be determined by an attending physician and can take into account compatibility of treatments and desired therapeutic effect to be achieved. It will be appreciated that therapeutically active agents utilized in combination may be administered together in a single composition, treatment or procedure, or alternatively may be administered separately.

EXAMPLES

Example 1

Inhibition of HIV Activity

1. Inhibition of HIV-mediated cell-cell fusion.

The inhibitory activities of the compounds on HIV-induced cell-cell fusion were determined using a dye transfer assay (Jiang S et al. Proc SPIE 3926:212-219, 2000). Briefly, H9/HIV-1$_{IIIB}$ cells were pre-labeled with a fluorescent dye, Calcein AM (Molecular Probes, Inc.), and incubated with a testing compound at a graded concentration at 37° C. for 30 min in a 96-well cell culture plate. Then the CD4$^+$ MT-2 cells were added to the H9/HIV-1$_{IIIB}$ cells at a ratio of 10:1, followed by incubation at 37° C. for 2 hrs. The fused and unfused calcein-labeled HIV-1-infected cells were counted under an inverted fluorescence microscope with an eyepiece micrometer disc. The percent inhibition of cell fusion by a compound and the $EC_{50}$ and $EC_{90}$ values were calculated using the software CalcuSyn.

2. Inhibition of HIV infection as measured by luciferase assay. The inhibitory activity of fusion/entry inhibitors on HIV infection in TZM-bl cells was determined by using a luciferase assay (Wei X et al. Antimicrob. Agents Chemother. 46:1896-1905, 2002). Briefly, 50 µl of a compound at graded concentration in triplicate were incubated with an equal volume of an HIV-1 isolate at 0.01 multiplicity of infection (MOI) at 37° C. for 30 min, followed by addition of the mixture to 100 µl TZM-bl cells (1×10$^5$/ml) that were pre-cultured in a 96-well plate at 37° C. overnight. After further culture at 37° C. for 3 days, the cells were harvested and lyzed with 50 µl lysing reagent. The luciferase activity was analyzed using a luciferase kit (Promega Corp.) and a luminometer (Model: Ultra 386, Tecan) according to the manufacture's instruction. The percent inhibition of cell fusion by a compound as well as $EC_{50}$ and $EC_{90}$ values were calculated using the software CalcuSyn.

3. Inhibition of HIV replication as measured by p24 antigen production. The inhibitory activity of fusion/entry inhibitors on HIV-1 infection as measured by p24 antigen production was determined as previously described (Zhao Q et al. AIDS Res Hum Retroviruses 18:989-997, 2002). In brief, 1×10$^4$ MT-2 cells were infected with an HIV-1 strain (100 TCID$_{50}$) in 200 µl RPMI 1640 medium containing 10% FBS in the presence or absence of testing compounds at graded concentrations overnight. Then the culture supernatants were removed and fresh media containing no testing compounds were added. On the fourth day post-infection, 100 µl of culture supernatants were collected from each well, mixed with equal volumes of 5% Triton X-100 and assayed for p24 antigen, which was quantitated by ELISA. Briefly, wells of polystyrene plates were coated with HIV immunoglobulin (HIVIG, prepared from plasma of HIV-seropositive donors with high neutralizing titers against HIV-1$_{IIIB}$), in 0.085 M carbonate-bicarbonate buffer (pH 9.6) at 4° C. overnight, followed by washes with washing buffer (0.01 M PBS containing 0.05% Tween-20) and blocking with PBS containing 1% dry fat-free milk. Virus lysates were added to the wells and incubated at 37° C. for 1 hr. After extensive washes, anti-p24 mAb (183-12H-5C), biotin labeled anti-mouse IgG1 (Santa Cruz Biotech), streptavidin-labeled horseradish peroxidase (Zymed), and the substrate 3,3',5,5'-tetramethylbenzidine (TMB, Sigma) were added sequentially. Reactions were terminated by addition of 1N $H_2SO_4$. Absorbance at 450 nm was recorded in an ELISA reader (Ultra 384, TECAN). Recombinant protein p24, purchased from US Biological, was included for establishing standard dose response curves. Each sample was tested in triplicate. The percentage of inhibition of p24 production was calculated as previously described (Neurath A R et al. BMC Infect Dis 2:6, 2002).

Inhibitory activity of fusion/entry inhibitors on infection by a primary HIV-1 isolate was determined as previously described (Jiang S et al. Antimicrob Agents Chemother 48:4349-4359, 2004). Peripheral blood mononuclear cells (PBMCs) were isolated from the blood of healthy donors by standard density gradient centrifugation using Histopaque-1077 (Sigma). The cells were plated in 75 $cm^2$ plastic flasks and incubated at 37° C. for 2 hrs. The nonadherent cells were collected and resuspended at $5 \times 10^6$ in 10 ml RPMI-1640 medium containing 10% FBS, 5 μg/ml PHA (phytohemagglutinin) and 100 U/ml IL-2 (Sigma), followed by incubation at 37° C. for 3 days. The PHA-stimulated cells were infected with a primary HIV-1 isolates at 0.01 MOI in the absence or presence of a compound at graded concentrations. Culture media were changed every 3 days. The supernatants were collected 7 days post-infection and tested for p24 antigen by ELISA as described above. The percent inhibition of p24 production and $EC_{50}$ values were calculated as described above.

4. Synergy analysis. The effective concentrations for 50, 70, 90 and 95% inhibition ($EC_{50}$, $EC_{70}$, $EC_{90}$, $EC_{95}$, respectively) are calculated and the inhibition data are analyzed for cooperative effects by using the CalcuSyn program for calculating the combination index (CI) as described (Chou T-C. The median-effect principle and the combination index for quantitation of synergism and antagonism. In: Chou T-C, Rideout DC (eds.), Synergism and Anatagonism in Chemotherpy. San Diego: Academic Press. 1991: 61-102). In all analyses, HIV fusion/entry inhibitors were assumed to act noncompetitively, which led to a more conservative estimate of synergy. CI values<1 and >1 indicate synergy and antagonism, respectively. Dose reductions were calculated as the compound concentrations required for inhibition of HIV-1 replication when the compound was used alone and in combination. The statistic analysis was performed by the One-Way Analysis of Variance (One-Way ANOVA) method using Origin 6.1 software.

5. Circular Dichroism (CD) Spectroscopy Analysis. CD measurements were performed as previously described (Lawless M K et al. Biochemistry 35:13697-13708, 1996). Briefly, N46 and each of the CHR-peptides were dissolved in PBS, pH 7.2. Individual peptides at 8 μM or mixtures of 8 μM of each peptide in PBS were incubated at 37° C. for 30 min. The CD spectrum of each sample was acquired on a Jasco spectropolarimeter (Model J-715, Jasco Inc., Japan) at 20° C. using a 5 nm bandwidth, 0.5 nm resolution, 0.1 cm path length, and an average time of 5.0 sec. Spectra were corrected by the subtraction of a blank corresponding to the solvent composition of each sample. Peptide interactions were determined according to Lawless's protocol by comparing the spectrum of the peptide mixture (experimental spectrum) to the sum of the individual spectra of the peptides at the same concentration and identical experimental condition (calculated noninteracting spectrum).

6. Enzyme-linked Immunosorbent Assay (ELISA). ELISA was used to determine the inhibitory activity of the C-peptides on the 6-HB core formation between N46 and biotinylated C34 (C34-biotin) with a conformation-specific monoclonal antibody (mAb) NC-1 (Jiang S et al. J Virol 72:10213-10217, 1998). Briefly, a testing peptide at 0.5 μM was preincubated with equal amount of N46 at 37° C. for 30 min, followed by the addition of C34-biotin (0.5 μM). The mixture was added to a 96-well polystyrene plate coated with mAb NC-1 IgG (2 μg/ml in 0.1M Tris, pH 8.8) and blocked with 2% non-fat milk in PBS. The plate was then incubated for 30 min and added to horseradish peroxidase (HRP) labeled with streptavidin (SA-HRP) (ZYMED Laboratories). The plate was washed with the washing buffer (PBS containing 0.01% Tween 20) for 6 times to remove any unbound peptide. The substrate TMB was added sequentially. Absorbance at 450 nm (A450) was measured using an ELISA reader. The percent inhibition of 6-HB formation and the $EC_{50}$ values were calculated using the CalcuSyn software.

Example 2

HIV Fusion/Entry Inhibitors Targeting Different Sites in the HIV-1

Figure 2:
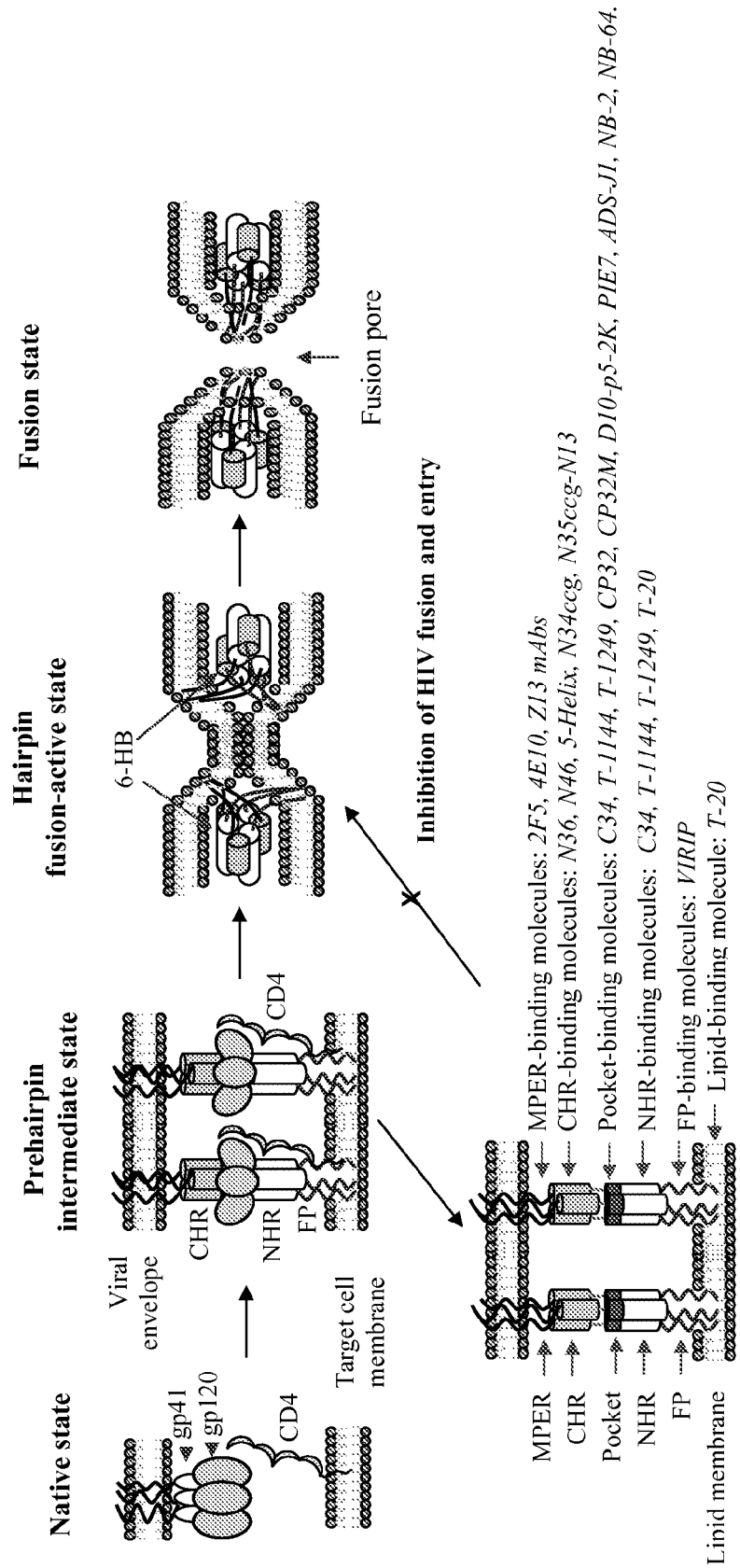
FIG. 2 depicts the target sites in the HIV-1 gp41 for HIV fusion/entry inhibitors.

The HIV-1 gp41 molecule consists the extracellular domain, transmembrane domain (TM) and cytoplasm domain (CP). The extracellular domain contains a fusion peptide (FP), N-terminal heptad repeat (NHR), and C-terminal heptad repeat (CHR). As shown in FIG. 1A, the NHR-peptide contains a pocket-forming domain (in bold), while the CHR-peptide contains a pocket-binding domain (PBD, in italic), a HR-binding domain (HBD), and a lipid-binding domain (LBD) or tryptophan-rich domain (TRD, underlined) in membrane-proximal external region (MPER). FIG. 1B depicts the interaction between the NHR- and CHR-peptides. The dashed lines between the NHR and CHR domains indicate the interaction between the residues located at the e, g and a, d positions in the NHR and CHR, respectively. The interaction between the PBD in the CHR-peptide and pocket-forming sequence in NHR-peptide is critical for stabilization of six-helix bundle formation and the pocket is an attractive target for HIV fusion/entry inhibitors (Chan D C et al. Proc Natl Acad Sci USA 95:15613-15617, 1998). Other regions in the gp41, including MPER, CHR, NHR, and FP can also serve as targets for anti-HIV drugs (FIG. 2 and Table 2).

TABLE 2

HIV fusion/entry inhibitors and their target sites in the HIV gp41

| HIV fusion/entry inhibitors | Targets in gp41 | | | | | Lipid membrane |
|---|---|---|---|---|---|---|
| | MPER | XCHR | Pocket | NHR | FP | |
| 2F5 mAb | + | | | | | |
| 4E10 mAb | + | | | | | |
| Z13 mAb | + | | | | | |
| N36 | | | | + | | |
| N46 | | | | + | | |
| 5-Helix | | | | + | | |
| N34ccg | | | | + | | |
| N35ccg-N13 | | | | + | | |
| HR121 | | | | + | | |

TABLE 2-continued

HIV fusion/entry inhibitors and their target sites in the HIV gp41

| HIV fusion/entry inhibitors | Targets in gp41 | | | | | Lipid membrane |
|---|---|---|---|---|---|---|
| | MPER | XCHR | Pocket | NHR | FP | |
| IQN17 | | + | | | | |
| ccIZN17 | | + | | | | |
| IZN28 | | + | | | | |
| IZN36 | | + | | | | |
| D10-p5-2K | | | + | | | |
| PIE7 | | | + | | | |
| ADS-J1 | | | + | | | |
| NB-2 | | | + | | | |
| NB-64 | | | + | | | |
| NB-206 | | | + | | | |
| D5 mAb | | | + | | | |
| CP32 | | | + | + | | |
| CP32M | | | + | + | | |
| C34 | | | + | + | | |
| T-1144 | | | + | + | | |
| Sifuvirtide | | | + | + | | |
| HR212 | | | + | + | | |
| T-1249 | | | + | + | | + |
| T-20 | | | | + | + | |
| VIRIP | | | | | + | |

Example 3

Figure 3A:
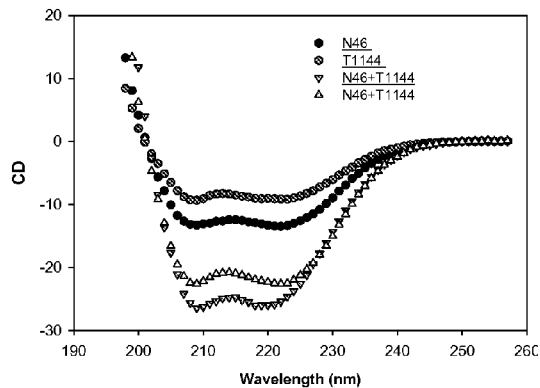
FIG. 3A: N46+T-1144.
Figure 3D:
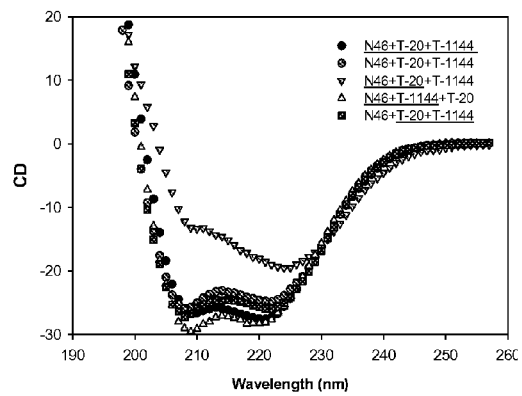
FIG. 3D: N46+T-20+T-1144.
Figure 3B:
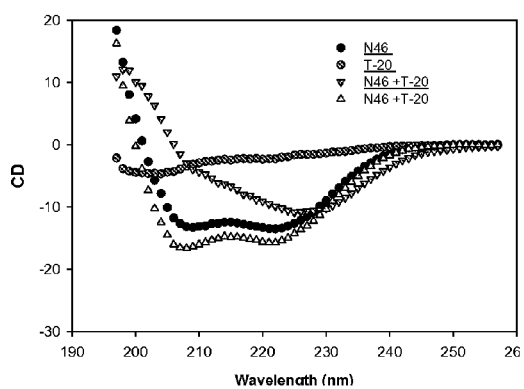
FIG. 3B: N46+T-20.
Figure 3E:
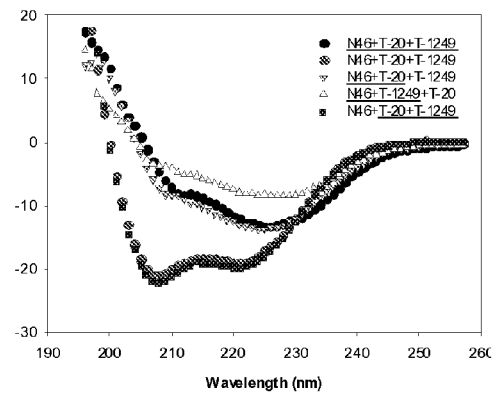
FIG. 3E: N46+T-20+T-1249.
Figure 3C:
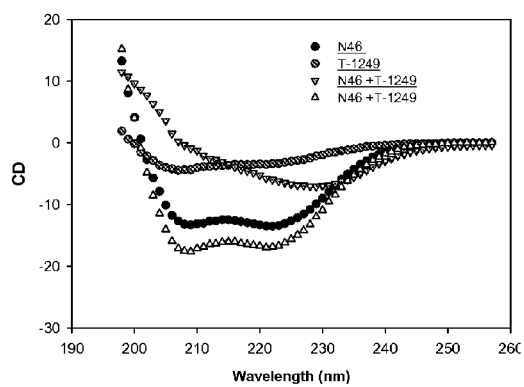
FIG. 3C: N46+T-1249.
Figure 3F:
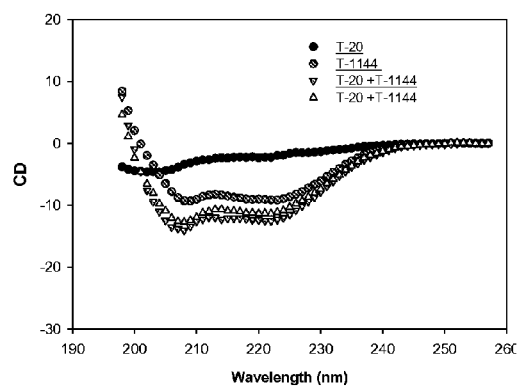
FIG. 3F: T-20+T-1144.

Analysis of the Interaction Between N46 and CHR-Peptide(s) by CD Spectroscopy To delineate the putative mechanism of synergism resulting from the combinations of HIV fusion/entry inhibitors, CD spectroscopy was used to study gp41 NHR and CHR interaction involving in secondary structure changes. CD spectra of single peptides and their mixtures were recorded under identical conditions. The spectra of the mixtures (experimental spectra) and the sum of the spectra of single peptides in the mixture (calculated noninteracting spectra) were compared to determine the interactions. If no structural changes occurred because of noninteraction in the mixture, identical experimental and calculated noninteracting spectra were expected. As shown in FIG. 3, the mixtures of N46 with T-1144, T-1249 and T-20, respectively, all displayed large secondary structure changes, indicating interactions between N46 and each of these CHR-peptides. N46 and T-1144, when mixed, formed typical α-helical complexes with increased α-helical content (FIG. 3A). T-20 and T-1249 were unstructured in solution with less than 20% helical content. When mixed with N46, instead of forming α-helical complex with increased helical content, T-20 and T-1249 significantly disrupted the α-helical conformation of N46 and resulted in a spectrum of a minimum at 228 nm (FIGS. 3B and C). This suggests that T-1249 and T-20 have a different interaction model with NHR from that of T-1144 with NHR. Subsequently, CD spectra of mixtures were recorded of N46 or PBS with two CHR peptides, T-20+T-1144 and T-20+T-1249, respectively. The noninteracting spectra were calculated in three ways to determine the interaction: i) sum of the spectra of three peptides (N46 and two CHR-peptides) measured separately; ii) sum of the spectra of two CHR-peptides measured separately; and iii) sum of the spectra of one peptide measured separately and two peptides measured in combination (underlined). As showed in FIGS. 3D and E, the experimental spectra of the triple mixtures did not overlap with the calculated noninteracting spectra of the corresponding mixtures, indicating interactions between N46 and the double combinations of the CHR-peptides. Interestingly, the calculated noninteracting spectra of N46+T-1144+T-20 and N46+T-20+T-1249 are similar to those of experimental spectra of N46+T-1144+T-20 and N46+T-20+T-1249, respectively. These data suggest that N46 and T-1144 interaction predominated in the N46/T-1144/T-20 mixture, while N46 and T-20 interaction was predominant in N46/T-20/T-1249 mixture. The CD signal changes from T-20 and T-1144 interaction is not significant (FIG. 3F). This further distinguishes the role of different peptide fusion/entry inhibitors administered in combination.

Example 4

Determination of Cooperative Effects of T-20 and T-1249 Combination on Inhibition of HIV-1-Mediated Cell-Cell Fusion The cooperative effects of T-20 and T-1249 on HIV-1-mediated cell-cell fusion was determined by using a dye-transfer assay. Each peptide was tested alone and in combination and their concentrations for causing 50% and 90% inhibition of the cell fusion were calculated and their cooperative effects were analyzed by using the CalcuSyn program for calculating the combination index (CI) (Chou T-C. The median-effect principle and the combination index for quantitation of synergism and antagonism. In: Chou T-C, Rideout D C eds., Synergism and Anatagonism in Chemotherapy. San Diego: Academic Press. 1991: 61-102). As shown in Table 3, the $EC_{90}$ values of T-20 and T-1249, tested alone, were 36.368 and 2.743 nM, respectively, whereas those of T-20 and T-1249, tested in combination, were 0.068 and 0.017 nM, respectively. The potency of T-20 and T-1249 in the combination was increased more than 534 and 160-fold, respectively, and the CI was 0.009. These results suggest that combinations of the first and second generation HIV fusion/entry inhibitors leads to exceptional synergistic anti-HIV activity.

TABLE 3

Combination index and potency increase for inhibition of HIV-1-mediated cell fusion by the combination of T-20 and T-1249.

| T-20:T-1249 (4:1) (Molecular ratio) | | T-20 | | | T-1249 | | |
|---|---|---|---|---|---|---|---|
| | CI | Concentration (nM) Alone | Mix | Potency increase (fold) | Concentration (nM) Alone | Mix | Potency increase (fold) |
| $EC_{50}$ | 0.013 | 19.799 | 0.038 | 521.026 | 1.559 | 0.010 | 155.900 |
| $EC_{70}$ | 0.011 | 26.830 | 0.051 | 526.078 | 2.068 | 0.013 | 159.077 |
| $EC_{90}$ | 0.009 | 36.368 | 0.068 | 534.824 | 2.743 | 0.017 | 161.353 |
| $EC_{95}$ | 0.008 | 44.735 | 0.082 | 545.549 | 3.324 | 0.021 | 158.286 |

*CI = Combination index value

Example 5

Determination of Cooperative Effects of T-20 and T-1144 Combination on Inhibition of HIV-1-Mediated Cell-Cell Fusion The cooperative effects of T-20 and T-1144 on HIV-1-mediated cell-cell fusion was determined as described in Example 4. As shown in the Table 4, the $EC_{90}$ values of T-20 and T-1144, tested alone, were 36.368 and 4.834 nM, respectively, whereas those of T-20 and T-1249, tested in combination, were 0.043 and 0.011 nM, respectively. The potency of T-20 and T-1144 in the combination was increased more than 845- and 438-fold, respectively, and the CI was 0.004. These results suggest that combination of the first and third generation HIV fusion/entry inhibitors leads to exceptional synergistic anti-HIV activity.

TABLE 4

Combination index and potency increase for inhibition of HIV-1-mediated cell fusion by the combination of T-20 and T-1144.

| T-20:T-1144 (4:1) (Molecular ratio) | | T-20 | | | T-1144 | | |
|---|---|---|---|---|---|---|---|
| | CI | Concentration (nM) Alone | Mix | Potency increase (fold) | Concentration (nM) Alone | Mix | Potency increase (fold) |
| $EC_{50}$ | 0.006 | 19.799 | 0.025 | 791.960 | 2.613 | 0.006 | 435.500 |
| $EC_{70}$ | 0.005 | 26.830 | 0.033 | 813.030 | 3.554 | 0.008 | 444.250 |
| $EC_{90}$ | 0.004 | 36.368 | 0.043 | 845.767 | 4.834 | 0.011 | 439.455 |
| $EC_{95}$ | 0.003 | 44.735 | 0.052 | 860.288 | 5.960 | 0.013 | 458.462 |

Example 6

Determination of Cooperative Effects of T-20 and C34 Combination on Inhibition of HIV-1-Mediated Cell-Cell Fusion The cooperative effects of T-20 and C34 on HIV-1-mediated cell-cell fusion was determined as described in Example 4. As shown in the Table 5, the $EC_{90}$ values of T-20 and C34, tested alone, were 36.368 and 2.518 nM, respectively, whereas those of T-20 and C34, tested in combination, were 0.564 and 0.071 nM, respectively. The potency of T-20 and C34 in the combination was increased more than 63- and 34-fold, respectively, and the CI was 0.039. These results suggest that the combination of T-20 and C34 leads to significant synergistic anti-HIV activity.

TABLE 5

Combination index and potency increase for inhibition of HIV-1-mediated cell fusion by the combination of T-20 and C34.

| T-20:C34 (8:1) (Molecular ratio) | | T-20 | | | C34 | | |
|---|---|---|---|---|---|---|---|
| | CI | Concentration (nM) Alone | Mix | Potency increase (fold) | Concentration (nM) Alone | Mix | Potency increase (fold) |
| $EC_{50}$ | 0.040 | 19.799 | 0.324 | 61.108 | 1.465 | 0.041 | 35.732 |
| $EC_{70}$ | 0.040 | 26.830 | 0.427 | 62.834 | 1.920 | 0.053 | 36.226 |
| $EC_{90}$ | 0.039 | 36.368 | 0.564 | 64.482 | 2.518 | 0.071 | 35.465 |
| $EC_{95}$ | 0.039 | 44.735 | 0.682 | 65.594 | 3.028 | 0.085 | 35.624 |

Example 7

Determination of Cooperative Effects of T-1249 and T-1144 Combination on Inhibition of HIV-1-Mediated Cell-Cell Fusion The cooperative effects of T-1249 and T-1144 on HIV-1-mediated cell-cell fusion was determined as described in Example 4. As shown in the Table 6, the $EC_{90}$ values of T-1249 and T-1144, tested alone, were 2.743 and 4.834 nM, respectively, whereas those of T-1249 and T-1144, tested in combination, were 0.308 and 0.308 nM, respectively. The potency of T-1249 and T-1144 in the combination was increased more than 8- and 15-fold, respectively, and the CI was 0.091. These results suggest that combinations of the second and third generation HIV fusion/entry inhibitors leads to significant synergistic anti-HIV activity.

TABLE 6

Combination index and potency increase for inhibition of HIV-1-mediated cell fusion by the combination of T-1249 and T-1144.

| T-1249:T-1144 (1:1) (Molecular ratio) | | T-1249 | | | T-1144 | | |
|---|---|---|---|---|---|---|---|
| | CI | Concentration (nM) Alone | Mix | Potency increase (fold) | Concentration (nM) Alone | Mix | Potency increase (fold) |
| $EC_{50}$ | 0.092 | 1.559 | 0.174 | 8.960 | 2.613 | 0.174 | 15.017 |
| $EC_{70}$ | 0.091 | 2.068 | 0.232 | 8.914 | 3.554 | 0.232 | 15.319 |
| $EC_{90}$ | 0.091 | 2.743 | 0.308 | 8.906 | 4.834 | 0.308 | 15.695 |
| $EC_{95}$ | 0.090 | 3.324 | 0.374 | 8.888 | 5.960 | 0.374 | 15.936 |

Example 8

Determination of Cooperative Effects of T-1249 and C34 Combination on Inhibition of HIV-1-Mediated Cell-Cell Fusion The cooperative effects of T-1249 and C34 on HIV-1-mediated cell-cell fusion was determined as described in Example 4. As shown in the Table 7, the $EC_{90}$ values of T-1249 and C34, tested alone, were 2.743 and 2.518 nM, respectively, whereas those of T-1249 and C34, tested in combination, were 0.256 and 0.128 nM, respectively. The potency of T-1249 and C34 in the combination was increased more than 10- and 19-fold, respectively, and the CI was 0.149. These results suggest that combination of the second and third generation HIV fusion/entry inhibitors leads to significant synergistic anti-HIV activity.

TABLE 7

Combination index and potency increase for inhibition of HIV-1-mediated cell fusion by the combination of T-1249 and C34.

| T-1249:C34 (2:1) (Molecular ratio) | | T-1249 | | | C34 | | |
|---|---|---|---|---|---|---|---|
| | CI | (Concentration (nM) (Alone | Mix | Potency increase (fold) | Concentration (nM) Alone | Mix | Potency increase (fold) |
| $EC_{50}$ | 0.212 | 1.559 | 0.139 | 11.216 | 1.465 | 0.070 | 20.929 |
| $EC_{70}$ | 0.178 | 2.068 | 0.189 | 10.942 | 1.920 | 0.095 | 20.211 |
| $EC_{90}$ | 0.149 | 2.743 | 0.256 | 10.715 | 2.518 | 0.128 | 19.672 |
| $EC_{95}$ | 0.132 | 3.324 | 0.315 | 10.552 | 3.028 | 0.158 | 19.165 |

Example 9

Determination of Cooperative Effects of T-1144 and C34 Combination on Inhibition of HIV-1-Mediated Cell-Cell Fusion The cooperative effects of T-1144 and C34 on HIV-1-mediated cell-cell fusion was determined as described in Example 4. As shown in the Table 8, the EC90 values of T-1144 and C34, tested alone, were 4.834 and 2.518 nM, respectively, whereas those of T-1144 and C34, tested in combination, were 0.543 and 0.272 nM, respectively. The potency of T-1144 and C34 in the combination was increased more than 8- and 8-fold, respectively, and the CI was 0.208. These results suggest that combinations of the second and third generation HIV fusion/entry inhibitors leads to significant synergistic anti-HIV activity.

TABLE 8

Combination index and potency increase for inhibition of HIV-1-mediated cell fusion by the combination of T-1144 and C34.

| T-1144:C34 (2:1) (Molecular ratio) | | T-1144 | | | C34 | | |
|---|---|---|---|---|---|---|---|
| | CI | Concentration (nM) | | Potency increase (fold) | Concentration (nM) | | Potency increase (fold) |
| | | Alone | Mix | | Alone | Mix | |
| $EC_{50}$ | 0.288 | 2.613 | 0.307 | 8.511 | 1.465 | 0.154 | 9.513 |
| $EC_{70}$ | 0.244 | 3.554 | 0.408 | 8.711 | 1.920 | 0.204 | 9.412 |
| $EC_{90}$ | 0.208 | 4.834 | 0.543 | 8.902 | 2.518 | 0.272 | 9.257 |
| $EC_{95}$ | 0.186 | 5.960 | 0.659 | 9.044 | 3.028 | 0.330 | 9.176 |

Example 10

Determination of Cooperative Effects of T-20, T-1249 and T-1144 Combination on Inhibition of HIV-1-Mediated Cell-Cell Fusion The cooperative effects of T-20, T-1249 and T-1144 on HIV-1-mediated cell-cell fusion was determined. As shown in the Table 9, the $EC_{90}$ values of T-20, T-1249 and T-1144, tested alone, were 36.368, 2.743, and 4.834 nM, respectively, whereas those of T-20, T-1249 and T-1144, tested in combination, were 0.025, 0.006 and 0.006 nM, respectively. The potency of T-20, T-1249 and T-1144 in the combination was increased more than 1454-, 456- and 805-fold, respectively, and the CI was 0.002. These results suggest that combinations of the first, second and third generation HIV fusion/entry inhibitors leads to exceptional synergistic anti-HIV activity.

Example 11

Determination of Co-Action of T-20, T-1249 and C34 Combination on Inhibition of HIV-1-Mediated Cell-Cell Fusion The cooperative effects of T-20, T-1249 and C34 on HIV-1-mediated cell-cell fusion was determined. As shown in the Table 10, the $EC_{90}$ values of T-20, T-1249 and C34 when tested alone were 36.368, 2.743, and 2.518 nM, respectively, whereas those of T-20, T-1249 and C34 when tested in combination were 0.091, 0.023 and 0.011 nM, respectively. The potency of T-20, T-1249 and C34 in the combination was increased more than 399-, 118- and 228-fold, respectively, and the CI was 0.014. These results suggest that combinations of T-20, T-1249 and C34 lead to exceptional synergistic anti-HIV activity.

TABLE 10

Combination index and potency increase for inhibition of HIV-1-mediated cell fusion by the combination of T-20, T-1249 and C34

| T-20:T-1249:C34 (8:2:1) (Molecular ratio) | | T20 | | | T-1249 | | | C34 | | |
|---|---|---|---|---|---|---|---|---|---|---|
| | CI | Concentration (nM) | | Potency increase (fold) | Concentration (nM) | | Potency increase (fold) | Concentration (nM) | | Potency increase (fold) |
| | | Alone | Mix | | Alone | Mix | | Alone | Mix | |
| $EC_{50}$ | 0.015 | 19.799 | 0.054 | 366.648 | 1.559 | 0.013 | 119.923 | 1.465 | 0.007 | 209.286 |
| $EC_{70}$ | 0.015 | 26.830 | 0.070 | 383.286 | 2.068 | 0.017 | 121.647 | 1.920 | 0.009 | 213.333 |
| $EC_{90}$ | 0.014 | 36.368 | 0.091 | 399.648 | 2.743 | 0.023 | 119.261 | 2.518 | 0.011 | 228.909 |
| $EC_{95}$ | 0.012 | 44.735 | 0.108 | 414.213 | 3.324 | 0.027 | 123.111 | 3.028 | 0.014 | 216.286 |

Example 12

Determination of Cooperative Effects of T-20 and Sifuvirtide Combination on Inhibition of HIV-1-Mediated Cell-Cell Fusion The cooperative effects of T-20 and sifuvirtide on HIV-1-mediated cell-cell fusion was determined by using a dye-transfer assay. Each peptide was tested alone and in combination and their concentrations for causing 50% and 90% inhibition of the cell fusion were calculated and their cooperative effects were analyzed by using the CalcuSyn program for calculating the CI as described above. As shown in the Table 11, the $EC_{90}$ values of T-20 and sifuvirtide when tested alone were 26.404 and 26.078 nM, respectively, whereas those of T-20 and sifuvirtide when tested in combination were

TABLE 9

Combination index and potency increase for inhibition of HIV-1-mediated cell fusion by the combination of T-20, T-1249 and T-1144.

| T-20:T-1249:T-1144 (4:1:1) (Molecular ratio) | | T-20 | | | T-1249 | | | T-1144 | | |
|---|---|---|---|---|---|---|---|---|---|---|
| | CI | Concentration (nM) | | Potency increase (fold) | Concentration (nM) | | Potency increase (fold) | Concentration (nM) | | Potency increase (fold) |
| | | Alone | Mix | | Alone | Mix | | Alone | Mix | |
| $EC_{50}$ | 0.004 | 19.799 | 0.015 | 1319.933 | 1.559 | 0.004 | 389.750 | 2.613 | 0.004 | 653.250 |
| $EC_{70}$ | 0.003 | 26.830 | 0.019 | 1412.105 | 2.068 | 0.005 | 413.600 | 3.554 | 0.005 | 710.800 |
| $EC_{90}$ | 0.002 | 36.368 | 0.025 | 1454.720 | 2.743 | 0.006 | 457.167 | 4.834 | 0.006 | 805.667 |
| $EC_{95}$ | 0.002 | 44.735 | 0.029 | 1542.586 | 3.324 | 0.007 | 474.857 | 5.960 | 0.007 | 851.429 |

3.001 and 0.750 nM, respectively. The potency of T-20 and Sifuvirtide in the combination was increased more than 8- and 34-fold, respectively, and the CI was 0.107. These results suggest that combinations of T-20 and C34 leads to significant synergistic anti-HIV activity.

TABLE 11

Combination index and potency increase for inhibition of HIV-1-medited cell fusion by combination of T-20 and sifuvirtide.

| T-20:Sifuvirtide (4:1) | | T-20 | | | Sifuvirtide | | |
|---|---|---|---|---|---|---|---|
| | | Concentration (nM) | | Potency increase | Concentration (nM) | | Potency increase |
| (Molecular ratio) | CI | Alone | Mix | (fold) | Alone | Mix | (fold) |
| $EC_{50}$ | 0.097 | 16.516 | 1.850 | 8.928 | 16.366 | 0.462 | 35.424 |
| $EC_{70}$ | 0.102 | 20.882 | 2.356 | 8.863 | 20.659 | 0.589 | 35.075 |
| $EC_{90}$ | 0.107 | 26.404 | 3.001 | 8.798 | 26.078 | 0.750 | 34.771 |
| $EC_{95}$ | 0.111 | 30.973 | 3.537 | 8.757 | 30.555 | 0.884 | 34.564 |

Example 13

Determination of Cooperative Effects of T-20, T-1249, and T-1144 Combinations on Inhibition of Infection by Laboratory-Adapted and Primary HIV-1 Strains The cooperative effects of T-20, T-1249 and/or T-1144 on infection by two laboratory-adapted HIV-1 strains, IIIB (subtype B, X4) and BaL (subtype B, R5), and two primary HIV-1 isolates, 931N101 (subtype C, R5) and RU570 (clade G, R5) was determined. Synergism was observed for all virus strains tested. Double combination of T-20 with T-1249 or T-1144 resulted in dose reduction of about 3- to 12-fold or 5- to 20-fold, respectively, for inhibiting infection by laboratory-adapted HIV-1 strains. Strikingly, a triple combination (T-20+ T-1249+T-1144) caused the greatest synergism with 71- to 281-fold dose reduction in inhibiting laboratory-adapted HIV-1 infection (Table 12). Potent synergism was also observed against infection by the primary HIV-1 isolates 931N101 and RU570 with double and triple combinations of T-20 with T-1249 and/or T-1144 (Table 12). Although double combinations of T-20 with T-1249 or T-1144 exhibited strong synergism against infection by both laboratory-adapted and primary HIV-1 strains, these data confirm that triple combinations lead to even stronger synergism.

Example 14

Determination of Cooperative Effects of T-20, T-1249, and T-1144 Combinations on Inhibition of Infection by T-20-Resistant HIV-1 Strains The cooperative effects of T-20, T-1249, and T-1144 on inhibition of infection by T-20-sensitive strain, NL4-3$_{D36G}$, and three T-20-resistant strains, NL4-3$_{(36G)V38A}$, NL4-3$_{(36G)V38A/N42D}$, and NL4-3$_{(36G)V38E/N42S}$, which contain a single or double mutation in the principal determinant of T-20 resistance (aa 36-45: GIVQQQNNLL; SEQ ID NO:55) in the gp41 NHR domain, including V38A, V38A/ N42D, and V38E/N42S, was determined. Each peptide was tested alone and in combination and their concentrations for causing 50% inhibition of the cell fusion were calculated and their cooperative effects were analyzed by using the CalcuSyn program for calculating the CI as described above. As shown in Table 13, when tested separately, T-20, T-1249 and T-1144 were effective against the T-20-sensitive strain, NL4-3$_{D36G}$, with $EC_{50}$ ranging from 6-49 nM. However, T-20 could only inhibit infection by these three T-20-resistant variants at high concentration ($EC_{50}$=313, 2,646, and 9,894 nM) for inhibiting infection by NL4-3$_{(36G)V38A}$, NL4-3$_{(36G)V38A/N42D}$, and NL4-3$_{(36G)V38E/N42S}$, respectively), while T-1144 was highly effective against all three T-20-resistant viruses with $EC_{50}$ about 4-6 nM. Interestingly, both NL4-3$_{(36G)V36A}$ and NL4-3$_{(36G)V36A/N42D}$ were sensitive to T-1249 ($EC_{50}$=4-10 nM), but NL4-3$_{(36G)V38E/N42S}$ was resistant to T-1249 ($EC_{50}$=358 nM). However, the double combination of T-20 and T-1249 or T-1144 resulted in significant synergistic activity against T-20- and T-1249-resistant strains with 2- to 26-fold dose reduction. Consistent with the results of testing laboratory-adapted HIV-1 strains, stronger synergism was observed in triple combination of these peptides against these T-20- and T-1249-resistant strains with 9- to 68-fold dose reduction. These results suggest that combining T-20 with T-1249 and/or T-1144 results in highly potent synergistic activity against both T-20- and T-1249-resistant HIV-1 strains, suggesting a new therapeutic strategy for the treatment of patients who have failed to respond to T-20 monotherapy.

Example 15

Figure 4A:
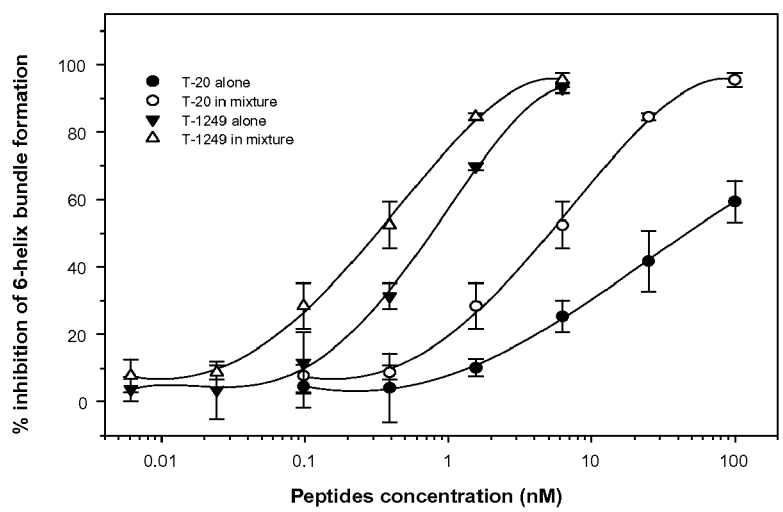
FIG. 4A: T-20+T-1249.
Figure 4B:
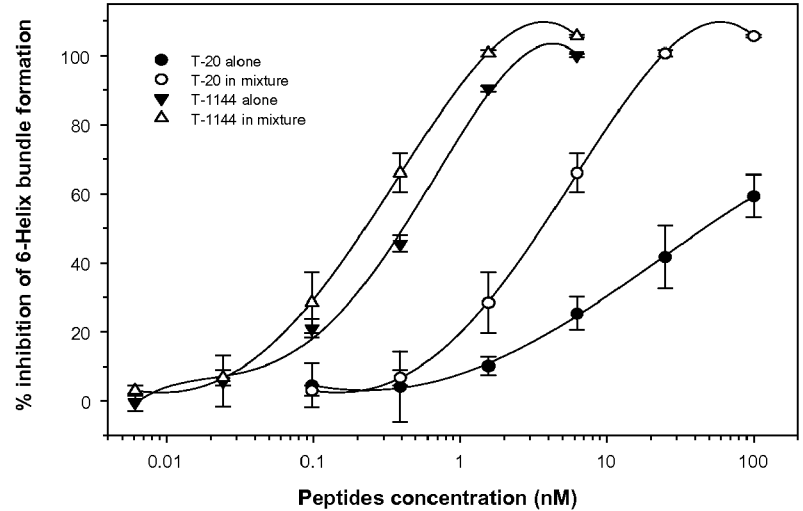
FIG. 4B: T-20+T-1144.
Figure 4C:
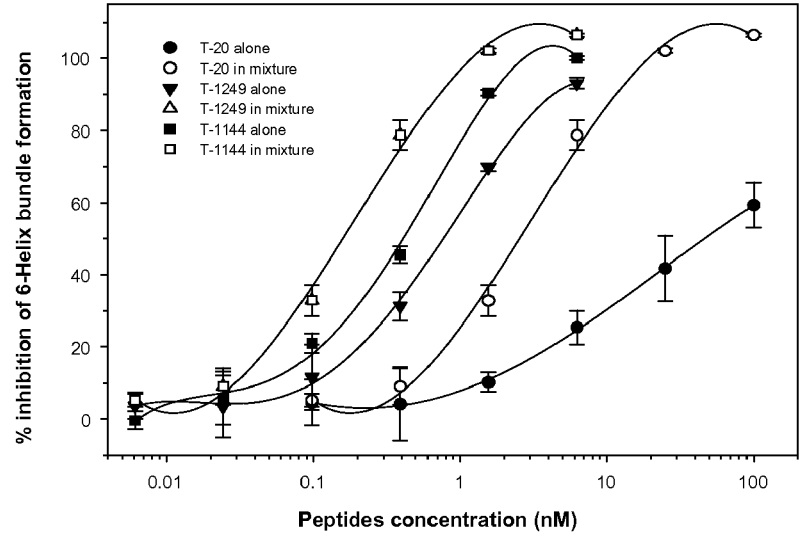
FIG. 4C: T-20+T-1249+T-1144.

Determination of Cooperative Effects of T-20, T-1249, and T-1144 Combinations on Inhibition of the Gp41 Six-Helix Bundle Core Formation Combining T-20 with T-1249 and/or T-1144 resulted in synergistic effect on six-helix bundle core formation. Subsequently, we determined the potential synergism resulting from the combination of T-20 with T-1249 and/or T-1144 against six-helix bundle formation between N46 and C34-biotin. T-20 alone could only weakly inhibit six-helix bundle formation with $EC_{50}$ of 59 µM, while T-1249 and T-1144 alone significantly blocked six-helix bundle formation in a dose-dependent manner with $EC_{50}$ of 0.8 and 0.3 µM, respectively. Combining T-20 and T-1249 (FIG. 4A) or T-20 and T-1144 (FIG. 4B) resulted in synergistic effect on inhibition of six-helix bundle formation with CI of 0.4 and 0.5, respectively. Triple combination also showed synergism with dose reduction of T-20, T-1249, and T-1144 about 26-, 4-, and 2-fold, respectively (FIG. 4C). These results suggest that the increased potency of these CHR-peptides in combination against HIV-1 Env-mediated membrane fusion is because of their synergistic effect on inhibition of the gp41 six-helix bundle core formation.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

TABLE 12

Combination index (CI) and dose reduction in inhibition of infection by laboratory-adapted and primary HIV-1 strains by combining T-20 with T-1249 and/or T-1144.

| Combination | | T-20 | | | T-1249 | | |
|---|---|---|---|---|---|---|---|
| Viruses | | $EC_{50}$ (nM) | | Dose | $EC_{50}$ (nM) | | Dose |
| (subtype, tropism) | CI | alone | in mixture | reduction (fold) | alone | in mixture | reduction (fold) |
| IIIB (B, X4) | 0.44 | 50.44 | 15.21 | 3.32 | 19.20 | 3.80 | 5.05 |
| Bal (B, R5) | 0.13 | 8.42 | 0.73 | 11.53 | 3.91 | 0.36 | 10.86 |
| 93IN101 (C, R5)* | 0.16 | 39.89 | 3.66 | 10.90 | 13.58 | 0.91 | 14.92 |
| RU570 (G, R5)* | 0.23 | 38.44 | 5.98 | 6..43 | 19.15 | 1.50 | 12.77 |

| | | T-20 | | | T-1144 | | |
|---|---|---|---|---|---|---|---|
| Viruses | | $EC_{50}$ (nM) | | Dose | | $EC_{50}$ (nM) | Dose |
| (subtype, tropism) | CI | alone | in mixture | reduction (fold) | reduction (fold) | in mixture | reduction (fold) |
| IIIB (B, X4) | 0.31 | 50.44 | 9.88 | 5.11 | 4.95 | 0.62 | 7.98 |
| Bal (B, R5) | 0.06 | 8.42 | 0.42 | 20.05 | 4.18 | 0.21 | 19.90 |
| 93IN101 (C, R5)* | 0.18 | 39.89 | 4.29 | 9.30 | 15.47 | 1.07 | 14.46 |
| RU570 (G, R5)* | 0.19 | 38.44 | 5.19 | 7.41 | 24.20 | 1.30 | 18.62 |

| Combination | | T-20 | | | T-1249 | | | T-1144 | | |
|---|---|---|---|---|---|---|---|---|---|---|
| Virus | | $EC_{50}$ (nM) | | Dose | $EC_{50}$ (nM) | | Dose | $EC_{50}$ (nM) | | Dose |
| (subtype, tropism) | CI | alone | in mixture | reduction (fold) | alone | in mixture | reduction (fold) | alone | in mixture | reduction (fold) |
| IIIB (B, X4) | 0.06 | 50.44 | 0.71 | 71.04 | 19.20 | 0.18 | 106.67 | 4.95 | 0.05 | 99.00 |
| Bal (B, R5) | 0.01 | 8.42 | 0.03 | 280.67 | 3.91 | 0.02 | 195.50 | 4.18 | 0.02 | 209.00 |
| 93IN101 (C, R5)* | 0.15 | 39.89 | 2.54 | 15.70 | 13.58 | 0.64 | 21.22 | 15.47 | 0.64 | 24.17 |
| RU570 (G, R5)* | 0.22 | 38.44 | 4.54 | 8.47 | 19.15 | 1.14 | 16.80 | 24.20 | 1.14 | 21.23 |

*Primary HIV-1 isolates; data are representative of two separate experiments. Each sample was tested in triplicate, and the mean values were presented. Ratios of the peptides in combinations: T-20:T-1249:T-1144 = 16:4:1 for IIIB; 2:1:1 for Bal; 4:1:1 for 93IN101 and RU650, respectively.

TABLE 13

Synergistic effect of combinations of T-20 with T-1249 and/or T-1144 on inhibition of infection by T-20-sensitive and-resistant HIV-1 strains*

| | | T-20 | | | T-1249 | | |
|---|---|---|---|---|---|---|---|
| NL4-3 | | $EC_{50}$ (nM) | | Dose | $EC_{50}$ (nM) | | Dose |
| mutants | CI | alone | in mixture | reduction (fold) | alone | in mixture | reduction (fold) |
| D36G | 0.46 | 48.76 | 7.52 | 6.48 | 17.45 | 5.37 | 3.25 |
| (36G)V38A | 0.06 | 313.04 | 13.59 | 23.03 | 4.35 | 0.17 | 25.59 |
| (36G)V38A/N42D | 0.38 | 2645.98 | 228.83 | 11.56 | 10.36 | 2.86 | 3.62 |
| (36G)V38E/N42S | 0.21 | 9894.46 | 732.6 | 13.51 | 358.01 | 48.84 | 7.33 |

| | | T-20 | | | T-1144 | | |
|---|---|---|---|---|---|---|---|
| NL4-3 | | $EC_{50}$ (nM) | | Dose | $EC_{50}$ (nM) | | Dose |
| mutants | CI | alone | in mixture | reduction (fold) | alone | in mixture | reduction (fold) |
| D36G | 0.26 | 48.76 | 3.14 | 15.53 | 5.85 | 0.45 | 13.00 |
| (36G)V38A | 0.09 | 313.04 | 18.65 | 16.78 | 3.76 | 0.23 | 16.35 |
| (36G)V38A/N42D | 0.53 | 2645.98 | 200.89 | 13.17 | 4.57 | 2.51 | 1.82 |
| (36G)V38E/N42S | 0.62 | 9894.46 | 3749.09 | 2.64 | 5.21 | 1.25 | 4.17 |

TABLE 13-continued

Synergistic effect of combinations of T-20 with T-1249 and/or T-1144 on inhibition of infection by T-20-sensitive and-resistant HIV-1 strains*

| NL4-3 mutants | CI | T-20 | | | T-1249 | | | T-1144 | | |
|---|---|---|---|---|---|---|---|---|---|---|
| | | $EC_{50}$ (nM) | | Dose reduction (fold) | $EC_{50}$ (nM) | | Dose reduction (fold) | $EC_{50}$ (nM) | | Dose reduction (fold) |
| | | alone | in mixture | | alone | in mixture | | alone | in mixture | |
| D36G | 0.22 | 48.76 | 2.62 | 18.61 | 17.45 | 1.87 | 9.33 | 5.85 | 0.37 | 15.81 |
| (36G)V38A | 0.07 | 313.04 | 8.29 | 37.76 | 4.35 | 0.10 | 43.50 | 3.76 | 0.10 | 37.60 |
| (36G)V38A/N42D | 0.17 | 2645.98 | 38.97 | 67.90 | 10.36 | 0.49 | 21.14 | 4.57 | 0.49 | 9.33 |
| (36G)V38E/N42S | 0.14 | 9894.46 | 410.16 | 24.12 | 358.01 | 27.34 | 13.09 | 5.21 | 0.14 | 37.21 |

*NL4-3$_{D36G}$ is a T-20-sensitive strain, which is the parent strain used for generation of T-20-resistant mutants, including NL4-3$_{(36G)V38A}$, NL4-3$_{(36G)V38A/N42D}$ and NL4-3$_{(36G)V38E/N42S}$. NL4-3$_{(36G)V38E/N42S}$ is also resistant to T-1249. Ratios of the peptides in combinations: T-20:T-1249:T-1144 = 7:5:1 for NL4-3$_{D36G}$; 80:1:1 for NL4-3$_{(36G)V38A}$; 80:1:1 for NL4-3$_{(36G)V38A/N42D}$; and 3000:200:1 for NL4-3$_{(36G)V38E/N42S}$, respectively. Data are representative of two separate experiments. Each sample was tested in triplicate, and the mean values were presented.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. A pharmaceutical composition comprising a synergistic combination of two or more human immunodeficiency virus (HIV) fusion/entry inhibitors in amounts effective for treatment of HIV, wherein the HIV fusion/entry inhibitors are selected from the group consisting of T-20 (enfuvirtide), T-1249, T-1144, C34, and sifuvirtide.

2. The pharmaceutical composition of claim 1, wherein the HIV fusion/entry inhibitors comprise T-20 and T-1249.

3. The pharmaceutical composition of claim 1, wherein the HIV fusion/entry inhibitors comprise T-20 and T-1144.

4. The pharmaceutical composition of claim 1, wherein the HIV fusion/entry inhibitors comprise T-1249 and T-1144.

5. The pharmaceutical composition of claim 1, wherein the HIV fusion/entry inhibitors comprise T-20 and C34.

6. The pharmaceutical composition of claim 1, wherein the HIV fusion/entry inhibitors comprise T-1249 and C34.

7. The pharmaceutical composition of claim 1, wherein the HIV fusion/entry inhibitors comprise T-1144 and C34.

8. The pharmaceutical composition of claim 1, wherein the HIV fusion/entry inhibitors comprise T-20, T-1249, and T-1144.

9. The pharmaceutical composition of claim 1, wherein the HIV fusion/entry inhibitors comprise T-20, T-1249, and C34.

10. The pharmaceutical composition of claim 1, wherein the HIV fusion/entry inhibitors comprise T-20 and sifuvirtide.

* * * * *

SEQUENCE LISTING

```
<160> NUMBER OF SEQ ID NOS: 55

<210> SEQ ID NO 1
<211> LENGTH: 8
<212> TYPE: PRT
<213> ORGANISM: Human immunodeficiency virus

<400> SEQUENCE: 1

Trp Met Glu Trp Asp Arg Glu Ile
1               5
```

```
<210> SEQ ID NO 2
<211> LENGTH: 30
<212> TYPE: PRT
<213> ORGANISM: Human immunodeficiency virus

<400> SEQUENCE: 2

Asn Asn Tyr Thr Ser Leu Ile His Ser Leu Ile Glu Glu Ser Gln Asn
1               5                   10                  15

Gln Gln Glu Lys Asn Glu Gln Glu Leu Leu Glu Leu Asp Lys
            20                  25                  30

<210> SEQ ID NO 3
<211> LENGTH: 30
<212> TYPE: PRT
<213> ORGANISM: Human immunodeficiency virus

<400> SEQUENCE: 3

Glu Trp Asp Arg Glu Ile Asn Asn Tyr Thr Ser Leu Ile His Ser Leu
1               5                   10                  15

Ile Glu Glu Ser Gln Asn Gln Gln Glu Lys Asn Glu Gln Glu
            20                  25                  30

<210> SEQ ID NO 4
<211> LENGTH: 28
<212> TYPE: PRT
<213> ORGANISM: Human immunodeficiency virus

<400> SEQUENCE: 4

Trp Met Glu Trp Asp Arg Glu Ile Asn Asn Tyr Thr Ser Leu Ile His
1               5                   10                  15

Ser Leu Ile Glu Glu Ser Gln Asn Gln Gln Glu Lys
            20                  25

<210> SEQ ID NO 5
<211> LENGTH: 34
<212> TYPE: PRT
<213> ORGANISM: Human immunodeficiency virus

<400> SEQUENCE: 5

Trp Met Glu Trp Asp Arg Glu Ile Asn Asn Tyr Thr Ser Leu Ile His
1               5                   10                  15

Ser Leu Ile Glu Glu Ser Gln Asn Gln Gln Glu Lys Asn Glu Gln Glu
            20                  25                  30

Leu Leu

<210> SEQ ID NO 6
<211> LENGTH: 35
<212> TYPE: PRT
<213> ORGANISM: Human immunodeficiency virus

<400> SEQUENCE: 6

Trp Glu Glu Trp Asp Lys Lys Ile Glu Glu Tyr Thr Lys Lys Ile Glu
1               5                   10                  15

Glu Leu Ile Lys Lys Ser Glu Glu Gln Gln Lys Lys Asn Glu Glu Glu
            20                  25                  30

Leu Lys Lys
        35

<210> SEQ ID NO 7
<211> LENGTH: 36
<212> TYPE: PRT
<213> ORGANISM: Human immunodeficiency virus
```

```
<400> SEQUENCE: 7

Ser Trp Glu Thr Trp Glu Arg Glu Ile Glu Asn Tyr Thr Lys Gln Ile
1               5                   10                  15

Tyr Lys Ile Leu Glu Glu Ser Gln Gln Gln Asp Arg Asn Glu Lys
            20                  25                  30

Asp Leu Leu Glu
        35

<210> SEQ ID NO 8
<211> LENGTH: 36
<212> TYPE: PRT
<213> ORGANISM: Human immunodeficiency virus

<400> SEQUENCE: 8

Trp Met Glu Trp Asp Arg Glu Ile Asn Asn Tyr Thr Ser Leu Ile His
1               5                   10                  15

Ser Leu Ile Glu Glu Ser Gln Asn Gln Gln Lys Asn Glu Gln Glu
            20                  25                  30

Leu Leu Glu Leu
        35

<210> SEQ ID NO 9
<211> LENGTH: 38
<212> TYPE: PRT
<213> ORGANISM: Human immunodeficiency virus

<400> SEQUENCE: 9

Thr Thr Trp Met Glu Trp Asp Arg Glu Ile Asn Asn Tyr Thr Ser Leu
1               5                   10                  15

Ile His Ser Leu Ile Glu Glu Ser Gln Asn Gln Gln Glu Lys Asn Glu
            20                  25                  30

Gln Glu Leu Leu Glu Leu
        35

<210> SEQ ID NO 10
<211> LENGTH: 38
<212> TYPE: PRT
<213> ORGANISM: Human immunodeficiency virus

<400> SEQUENCE: 10

Thr Thr Trp Glu Ala Trp Asp Arg Ala Ile Ala Glu Tyr Ala Ala Arg
1               5                   10                  15

Ile Glu Ala Leu Leu Arg Ala Leu Gln Glu Gln Gln Glu Lys Asn Glu
            20                  25                  30

Ala Ala Leu Arg Glu Leu
        35

<210> SEQ ID NO 11
<211> LENGTH: 38
<212> TYPE: PRT
<213> ORGANISM: Human immunodeficiency virus

<400> SEQUENCE: 11

Thr Thr Trp Glu Ala Trp Asp Arg Ala Ile Ala Glu Tyr Ala Ala Arg
1               5                   10                  15

Ile Glu Ala Leu Ile Arg Ala Ala Gln Glu Gln Gln Glu Lys Leu Glu
            20                  25                  30

Ala Ala Leu Arg Glu Leu
        35
```

```
<210> SEQ ID NO 12
<211> LENGTH: 38
<212> TYPE: PRT
<213> ORGANISM: Human immunodeficiency virus

<400> SEQUENCE: 12

Thr Thr Trp Glu Ala Trp Asp Arg Ala Ile Ala Glu Tyr Ala Ala Arg
1               5                   10                  15

Ile Glu Ala Leu Ile Arg Ala Ala Gln Glu Gln Gln Glu Lys Asn Glu
            20                  25                  30

Ala Ala Leu Arg Glu Leu
        35

<210> SEQ ID NO 13
<211> LENGTH: 43
<212> TYPE: PRT
<213> ORGANISM: Human immunodeficiency virus

<400> SEQUENCE: 13

Asn His Thr Thr Trp Met Glu Trp Asp Arg Glu Ile Asn Asn Tyr Thr
1               5                   10                  15

Ser Leu Ile His Ser Leu Ile Glu Glu Ser Gln Asn Gln Gln Glu Lys
            20                  25                  30

Asn Glu Gln Glu Leu Leu Glu Leu Asp Lys Trp
        35                  40

<210> SEQ ID NO 14
<211> LENGTH: 46
<212> TYPE: PRT
<213> ORGANISM: Human immunodeficiency virus

<400> SEQUENCE: 14

Trp Met Glu Trp Asp Arg Glu Ile Asn Asn Tyr Thr Ser Leu Ile His
1               5                   10                  15

Ser Leu Ile Glu Glu Ser Gln Asn Gln Gln Glu Lys Asn Glu Gln Glu
            20                  25                  30

Leu Leu Glu Leu Asp Lys Trp Ala Ser Leu Trp Asn Trp Phe
        35                  40                  45

<210> SEQ ID NO 15
<211> LENGTH: 55
<212> TYPE: PRT
<213> ORGANISM: Human immunodeficiency virus

<400> SEQUENCE: 15

Asn His Thr Thr Trp Met Glu Trp Asp Arg Glu Ile Asn Asn Tyr Thr
1               5                   10                  15

Ser Leu Ile His Ser Leu Ile Glu Glu Ser Gln Asn Gln Gln Glu Lys
            20                  25                  30

Asn Glu Gln Glu Leu Leu Glu Leu Asp Lys Trp Ala Ser Leu Trp Asn
        35                  40                  45

Trp Phe Asn Ile Lys Ile Leu
    50                  55

<210> SEQ ID NO 16
<211> LENGTH: 32
<212> TYPE: PRT
<213> ORGANISM: Human immunodeficiency virus

<400> SEQUENCE: 16

Gln Ile Trp Asn Asn Met Thr Trp Met Glu Trp Asp Arg Glu Ile Asn
```

-continued

```
1               5                   10                  15

Asn Tyr Thr Ser Leu Ile His Ser Leu Ile Glu Glu Ser Gln Asn Gln
            20                  25                  30

<210> SEQ ID NO 17
<211> LENGTH: 32
<212> TYPE: PRT
<213> ORGANISM: Human immunodeficiency virus

<400> SEQUENCE: 17

Val Glu Trp Asn Glu Met Thr Trp Met Glu Trp Glu Arg Glu Ile Glu
1               5                   10                  15
Asn Tyr Thr Lys Leu Ile Tyr Lys Ile Leu Glu Glu Ser Gln Glu Gln
            20                  25                  30

<210> SEQ ID NO 18
<211> LENGTH: 36
<212> TYPE: PRT
<213> ORGANISM: Human immunodeficiency virus

<400> SEQUENCE: 18

Trp Met Glu Trp Asp Arg Glu Ile Glu Glu Tyr Thr Lys Lys Ile Glu
1               5                   10                  15
Glu Tyr Thr Lys Lys Ile Glu Glu Tyr Thr Lys Lys Ile Glu Glu Tyr
            20                  25                  30

Thr Lys Lys Ile
        35

<210> SEQ ID NO 19
<211> LENGTH: 36
<212> TYPE: PRT
<213> ORGANISM: Human immunodeficiency virus

<400> SEQUENCE: 19

Trp Met Glu Trp Asp Arg Glu Ile Glu Glu Tyr Thr Lys Lys Ile Glu
1               5                   10                  15
Glu Tyr Thr Lys Lys Ile Glu Glu Tyr Thr Lys Lys Ile Glu Glu Tyr
            20                  25                  30

Thr Lys Lys Ile
        35

<210> SEQ ID NO 20
<211> LENGTH: 36
<212> TYPE: PRT
<213> ORGANISM: Human immunodeficiency virus

<400> SEQUENCE: 20

Trp Met Glu Trp Asp Arg Glu Ile Glu Glu Leu Ala Lys Lys Ala Glu
1               5                   10                  15
Glu Leu Ala Lys Lys Ala Glu Glu Leu Ala Lys Lys Ala Glu Glu Leu
            20                  25                  30

Ala Lys Lys Ala
        35

<210> SEQ ID NO 21
<211> LENGTH: 36
<212> TYPE: PRT
<213> ORGANISM: Human immunodeficiency virus

<400> SEQUENCE: 21

Trp Met Glu Trp Asp Arg Glu Ile Glu Glu Ala Ala Lys Lys Leu Glu
1               5                   10                  15
```

```
Glu Ala Ala Lys Lys Leu Glu Glu Ala Ala Lys Lys Leu Glu Glu Ala
            20                  25                  30

Ala Lys Lys Leu
        35

<210> SEQ ID NO 22
<211> LENGTH: 114
<212> TYPE: PRT
<213> ORGANISM: Human immunodeficiency virus

<400> SEQUENCE: 22

Trp Met Glu Trp Asp Arg Glu Ile Asn Asn Tyr Thr Ser Leu Ile His
1               5                   10                  15

Ser Leu Ile Glu Glu Ser Gln Asn Gln Gln Glu Lys Asn Glu Gln Glu
            20                  25                  30

Leu Leu Gly Gly Ser Gly Gly Ser Gly Ile Val Gln Gln Gln Asn Asn
        35                  40                  45

Leu Leu Arg Ala Ile Glu Ala Gln Gln His Leu Leu Gln Leu Thr Val
    50                  55                  60

Trp Gly Ile Lys Gln Leu Gln Ala Arg Ile Leu Gly Ser Ser Gly Gly
65                  70                  75                  80

Trp Met Glu Trp Asp Arg Glu Ile Asn Asn Tyr Thr Ser Leu Ile His
                85                  90                  95

Ser Leu Ile Glu Glu Ser Gln Asn Gln Gln Glu Lys Asn Glu Gln Glu
            100                 105                 110

Leu Leu

<210> SEQ ID NO 23
<211> LENGTH: 18
<212> TYPE: PRT
<213> ORGANISM: Human immunodeficiency virus

<400> SEQUENCE: 23

Lys Lys Gly Ala Cys Glu Ala Arg His Arg Glu Trp Ala Trp Leu Cys
1               5                   10                  15

Ala Ala

<210> SEQ ID NO 24
<211> LENGTH: 17
<212> TYPE: PRT
<213> ORGANISM: Human immunodeficiency virus

<400> SEQUENCE: 24

Lys Gly Ala Cys Glu Leu Leu Gly Trp Glu Trp Ala Trp Leu Cys Ala
1               5                   10                  15

Ala

<210> SEQ ID NO 25
<211> LENGTH: 15
<212> TYPE: PRT
<213> ORGANISM: Human immunodeficiency virus

<400> SEQUENCE: 25

Lys Gly Ala Cys Asp Tyr Pro Glu Trp Gln Trp Leu Cys Ala Ala
1               5                   10                  15

<210> SEQ ID NO 26
<211> LENGTH: 16
<212> TYPE: PRT
<213> ORGANISM: Human immunodeficiency virus
```

-continued

<400> SEQUENCE: 26

Ser Leu Glu Gln Ile Trp Asn Asn Met Thr Trp Met Gln Trp Asp Lys
1               5                   10                  15

<210> SEQ ID NO 27
<211> LENGTH: 8
<212> TYPE: PRT
<213> ORGANISM: Human immunodeficiency virus

<400> SEQUENCE: 27

Trp Ala Ser Leu Trp Asn Trp Phe
1               5

<210> SEQ ID NO 28
<211> LENGTH: 36
<212> TYPE: PRT
<213> ORGANISM: Human immunodeficiency virus

<400> SEQUENCE: 28

Tyr Thr Ser Leu Ile His Ser Leu Ile Glu Glu Ser Gln Asn Gln Gln
1               5                   10                  15

Glu Lys Asn Glu Gln Glu Leu Leu Glu Leu Asp Lys Trp Ala Ser Leu
            20                  25                  30

Trp Asn Trp Phe
            35

<210> SEQ ID NO 29
<211> LENGTH: 36
<212> TYPE: PRT
<213> ORGANISM: Human immunodeficiency virus

<400> SEQUENCE: 29

His Ser Leu Ile Glu Glu Ser Gln Asn Gln Gln Glu Lys Asn Glu Gln
1               5                   10                  15

Glu Leu Leu Glu Leu Asp Lys Trp Ala Ser Leu Trp Asn Trp Phe Asn
            20                  25                  30

Ile Thr Asn Trp
            35

<210> SEQ ID NO 30
<211> LENGTH: 36
<212> TYPE: PRT
<213> ORGANISM: Human immunodeficiency virus

<400> SEQUENCE: 30

Glu Glu Tyr Thr Lys Lys Ile Glu Glu Tyr Thr Lys Lys Ile Glu Glu
1               5                   10                  15

Tyr Thr Lys Lys Ile Glu Glu Tyr Thr Lys Lys Ile Trp Ala Ser Leu
            20                  25                  30

Trp Asn Trp Phe
            35

<210> SEQ ID NO 31
<211> LENGTH: 36
<212> TYPE: PRT
<213> ORGANISM: Human immunodeficiency virus

<400> SEQUENCE: 31

Glu Glu Leu Ala Lys Lys Ala Glu Glu Leu Ala Lys Lys Ala Glu Glu
1               5                   10                  15

Leu Ala Lys Lys Ala Glu Glu Leu Ala Lys Lys Ala Trp Ala Ser Leu

```
                    20                  25                  30

Trp Asn Trp Phe
        35

<210> SEQ ID NO 32
<211> LENGTH: 36
<212> TYPE: PRT
<213> ORGANISM: Human immunodeficiency virus

<400> SEQUENCE: 32

Glu Glu Ala Ala Lys Lys Leu Glu Glu Ala Ala Lys Lys Leu Glu Glu
1               5                   10                  15

Ala Ala Lys Lys Leu Glu Glu Ala Lys Lys Leu Trp Ala Ser Leu
                20                  25                  30

Trp Asn Trp Phe
        35

<210> SEQ ID NO 33
<211> LENGTH: 36
<212> TYPE: PRT
<213> ORGANISM: Human immunodeficiency virus

<400> SEQUENCE: 33

Glu Ala Leu Ala Lys Ala Ala Glu Ala Leu Ala Lys Ala Ala Glu Ala
1               5                   10                  15

Leu Ala Lys Ala Ala Glu Ala Leu Ala Lys Ala Ala Trp Ala Ser Leu
                20                  25                  30

Trp Asn Trp Phe
        35

<210> SEQ ID NO 34
<211> LENGTH: 39
<212> TYPE: PRT
<213> ORGANISM: Human immunodeficiency virus

<400> SEQUENCE: 34

Trp Gln Glu Trp Glu Gln Lys Ile Thr Ala Leu Leu Glu Gln Ala Gln
1               5                   10                  15

Ile Gln Gln Glu Lys Asn Glu Tyr Glu Leu Gln Lys Leu Asp Lys Trp
                20                  25                  30

Ala Ser Leu Trp Glu Trp Phe
        35

<210> SEQ ID NO 35
<211> LENGTH: 37
<212> TYPE: PRT
<213> ORGANISM: Human immunodeficiency virus

<400> SEQUENCE: 35

Trp Met Glu Trp Asp Arg Glu Ile Glu Glu Tyr Thr Lys Lys Ile Glu
1               5                   10                  15

Glu Tyr Thr Lys Lys Ile Glu Glu Tyr Thr Lys Lys Ile Trp Ala Ser
                20                  25                  30

Leu Trp Asn Trp Phe
        35

<210> SEQ ID NO 36
<211> LENGTH: 37
<212> TYPE: PRT
<213> ORGANISM: Human immunodeficiency virus

<400> SEQUENCE: 36
```

```
Trp Met Glu Trp Asp Arg Glu Ile Glu Leu Ala Lys Lys Ala Glu
1               5                   10                  15

Glu Leu Ala Lys Lys Ala Glu Leu Ala Lys Lys Ala Trp Ala Ser
            20                  25                  30

Leu Trp Asn Trp Phe
            35

<210> SEQ ID NO 37
<211> LENGTH: 37
<212> TYPE: PRT
<213> ORGANISM: Human immunodeficiency virus

<400> SEQUENCE: 37

Trp Met Glu Trp Asp Arg Glu Ile Glu Ala Ala Lys Lys Leu Glu
1               5                   10                  15

Glu Ala Ala Lys Lys Leu Glu Ala Ala Lys Lys Leu Trp Ala Ser
            20                  25                  30

Leu Trp Asn Trp Phe
            35

<210> SEQ ID NO 38
<211> LENGTH: 37
<212> TYPE: PRT
<213> ORGANISM: Human immunodeficiency virus

<400> SEQUENCE: 38

Trp Met Glu Trp Asp Arg Glu Ile Glu Ala Leu Ala Lys Ala Glu
1               5                   10                  15

Ala Leu Ala Lys Ala Ala Glu Ala Leu Ala Lys Ala Trp Ala Ser
            20                  25                  30

Leu Trp Asn Trp Phe
            35

<210> SEQ ID NO 39
<211> LENGTH: 34
<212> TYPE: PRT
<213> ORGANISM: Human immunodeficiency virus

<400> SEQUENCE: 39

Ser Gly Ile Val Gln Gln Gln Asn Asn Leu Leu Arg Ala Ile Glu Ala
1               5                   10                  15

Gln Gln His Leu Leu Gln Leu Thr Val Trp Gly Ile Lys Gln Leu Gln
            20                  25                  30

Ala Arg

<210> SEQ ID NO 40
<211> LENGTH: 36
<212> TYPE: PRT
<213> ORGANISM: Human immunodeficiency virus

<400> SEQUENCE: 40

Ser Gly Ile Val Gln Gln Gln Asn Asn Leu Leu Arg Ala Ile Glu Ala
1               5                   10                  15

Gln Gln His Leu Leu Gln Leu Thr Val Trp Gly Ile Lys Gln Leu Gln
            20                  25                  30

Ala Arg Ile Leu
            35

<210> SEQ ID NO 41
<211> LENGTH: 46
```

<212> TYPE: PRT
<213> ORGANISM: Human immunodeficiency virus

<400> SEQUENCE: 41

Thr Leu Thr Val Gln Ala Arg Gln Leu Leu Ser Gly Ile Val Gln Gln
1               5                   10                  15

Gln Asn Asn Leu Leu Arg Ala Ile Glu Ala Gln Gln His Leu Leu Gln
                20                  25                  30

Leu Thr Val Trp Gly Ile Lys Gln Leu Gln Ala Arg Ile Leu
            35                  40                  45

<210> SEQ ID NO 42
<211> LENGTH: 51
<212> TYPE: PRT
<213> ORGANISM: Human immunodeficiency virus

<400> SEQUENCE: 42

Gln Ala Arg Gln Leu Leu Ser Gly Ile Val Gln Gln Gln Asn Asn Leu
1               5                   10                  15

Leu Arg Ala Ile Glu Ala Gln Gln His Leu Leu Gln Leu Thr Val Trp
                20                  25                  30

Gly Ile Lys Gln Leu Gln Ala Arg Ile Leu Ala Val Glu Arg Tyr Leu
            35                  40                  45

Lys Gln Gln
    50

<210> SEQ ID NO 43
<211> LENGTH: 38
<212> TYPE: PRT
<213> ORGANISM: Human immunodeficiency virus

<400> SEQUENCE: 43

Asn Asn Leu Leu Arg Ala Ile Glu Ala Gln Gln His Leu Leu Gln Leu
1               5                   10                  15

Thr Val Trp Gly Ile Lys Gln Leu Gln Ala Arg Ile Leu Ala Val Glu
                20                  25                  30

Arg Tyr Leu Lys Asp Gln
            35

<210> SEQ ID NO 44
<211> LENGTH: 45
<212> TYPE: PRT
<213> ORGANISM: Human immunodeficiency virus

<400> SEQUENCE: 44

Arg Met Lys Gln Ile Glu Asp Lys Ile Glu Glu Ile Glu Ser Lys Gln
1               5                   10                  15

Lys Lys Ile Glu Asn Glu Ile Ala Arg Ile Lys Lys Leu Leu Gln Leu
                20                  25                  30

Thr Val Trp Gly Ile Lys Gln Leu Gln Ala Arg Ile Leu
            35                  40                  45

<210> SEQ ID NO 45
<211> LENGTH: 45
<212> TYPE: PRT
<213> ORGANISM: Human immunodeficiency virus

<400> SEQUENCE: 45

Cys Cys Gly Gly Ile Lys Lys Glu Ile Glu Ala Ile Lys Lys Glu Gln
1               5                   10                  15

Glu Ala Ile Lys Lys Lys Ile Glu Ala Ile Glu Lys Leu Leu Gln Leu

```
                    20                  25                  30

Thr Val Trp Gly Ile Lys Gln Leu Gln Ala Arg Ile Leu
            35                  40                  45

<210> SEQ ID NO 46
<211> LENGTH: 53
<212> TYPE: PRT
<213> ORGANISM: Human immunodeficiency virus

<400> SEQUENCE: 46

Ile Lys Lys Glu Ile Glu Ala Ile Lys Lys Glu Gln Glu Ala Ile Lys
1               5                   10                  15

Lys Lys Ile Glu Ala Ile Glu Lys Glu Ile Glu Ala Gln Gln His Leu
            20                  25                  30

Leu Gln Leu Thr Val Trp Gly Ile Lys Gln Leu Gln Ala Arg Ile Leu
            35                  40                  45

Ala Val Glu Arg Tyr
            50

<210> SEQ ID NO 47
<211> LENGTH: 62
<212> TYPE: PRT
<213> ORGANISM: Human immunodeficiency virus

<400> SEQUENCE: 47

Ile Lys Lys Glu Ile Glu Ala Ile Lys Lys Glu Gln Glu Ala Ile Lys
1               5                   10                  15

Lys Lys Ile Glu Ala Ile Glu Lys Glu Ile Ser Gly Ile Val Gln Gln
            20                  25                  30

Gln Asn Asn Leu Leu Arg Ala Ile Glu Ala Gln Gln His Leu Leu Gln
            35                  40                  45

Leu Thr Val Trp Gly Ile Lys Gln Leu Gln Ala Arg Ile Leu
            50                  55                  60

<210> SEQ ID NO 48
<211> LENGTH: 34
<212> TYPE: PRT
<213> ORGANISM: Human immunodeficiency virus

<400> SEQUENCE: 48

Ser Gly Ile Val Gln Gln Gln Asn Asn Leu Leu Arg Ala Ile Glu Ala
1               5                   10                  15

Gln Gln His Leu Leu Gln Leu Thr Val Trp Gly Ile Lys Gln Cys Cys
            20                  25                  30

Gly Arg

<210> SEQ ID NO 49
<211> LENGTH: 48
<212> TYPE: PRT
<213> ORGANISM: Human immunodeficiency virus

<400> SEQUENCE: 49

Ser Gly Ile Val Gln Gln Gln Asn Asn Leu Leu Arg Ala Ile Glu Ala
1               5                   10                  15

Gln Gln His Leu Leu Gln Leu Thr Val Trp Gly Ile Lys Gln Cys Cys
            20                  25                  30

Gly Arg Ile Ser Gly Ile Val Gln Gln Gln Asn Asn Leu Leu Arg Ala
            35                  40                  45

<210> SEQ ID NO 50
```

```
<211> LENGTH: 116
<212> TYPE: PRT
<213> ORGANISM: Human immunodeficiency virus

<400> SEQUENCE: 50

Ser Gly Ile Val Gln Gln Gln Asn Asn Leu Leu Arg Ala Ile Glu Ala
1               5                   10                  15

Gln Gln His Leu Leu Gln Leu Thr Val Trp Gly Ile Lys Gln Leu Gln
            20                  25                  30

Ala Arg Ile Leu Gly Ser Ser Gly Trp Met Glu Trp Asp Arg Glu
        35                  40                  45

Ile Asn Asn Tyr Thr Ser Leu Ile His Ser Leu Ile Glu Glu Ser Gln
50                  55                  60

Asn Gln Gln Glu Lys Asn Glu Gln Glu Leu Leu Gly Gly Ser Gly Gly
65                  70                  75                  80

Ser Gly Ile Val Gln Gln Gln Asn Asn Leu Leu Arg Ala Ile Glu Ala
                85                  90                  95

Gln Gln His Leu Leu Gln Leu Thr Val Trp Gly Ile Lys Gln Leu Gln
            100                 105                 110

Ala Arg Ile Leu
        115

<210> SEQ ID NO 51
<211> LENGTH: 216
<212> TYPE: PRT
<213> ORGANISM: Human immunodeficiency virus

<400> SEQUENCE: 51

Gln Leu Leu Ser Gly Ile Val Gln Gln Gln Asn Asn Leu Leu Arg Ala
1               5                   10                  15

Ile Glu Ala Gln Gln His Leu Leu Gln Leu Thr Val Trp Gly Ile Lys
            20                  25                  30

Gln Leu Gln Ala Arg Ile Leu Ala Gly Gly Ser Gly Gly His Thr Thr
        35                  40                  45

Trp Met Glu Trp Asp Arg Glu Ile Asn Asn Tyr Thr Ser Leu Ile His
50                  55                  60

Ser Leu Ile Glu Glu Ser Gln Asn Gln Gln Glu Lys Asn Glu Gln Glu
65                  70                  75                  80

Leu Leu Glu Gly Ser Ser Gly Gly Gln Leu Ser Gly Ile Val Gln
                85                  90                  95

Gln Gln Asn Asn Leu Leu Arg Ala Ile Glu Ala Gln Gln His Leu Leu
            100                 105                 110

Gln Leu Thr Val Trp Gly Ile Lys Gln Leu Gln Ala Arg Ile Leu Ala
        115                 120                 125

Gly Gly Ser Gly Gly His Thr Thr Trp Met Glu Trp Asp Arg Glu Ile
130                 135                 140

Asn Asn Tyr Thr Ser Leu Ile His Ser Leu Ile Glu Glu Ser Gln Asn
145                 150                 155                 160

Gln Gln Glu Lys Asn Glu Gln Glu Leu Leu Glu Gly Ser Ser Gly Gly
            165                 170                 175

Gln Leu Leu Ser Gly Ile Val Gln Gln Gln Asn Asn Leu Leu Arg Ala
        180                 185                 190

Ile Glu Ala Gln Gln His Leu Leu Gln Leu Thr Val Trp Gly Ile Lys
    195                 200                 205

Gln Leu Gln Ala Arg Ile Leu Ala
    210                 215
```

```
<210> SEQ ID NO 52
<211> LENGTH: 20
<212> TYPE: PRT
<213> ORGANISM: Human immunodeficiency virus

<400> SEQUENCE: 52

Leu Glu Ala Ile Pro Met Ser Ile Pro Pro Glu Val Lys Phe Asn Lys
1               5                   10                  15

Pro Phe Val Phe
            20

<210> SEQ ID NO 53
<211> LENGTH: 20
<212> TYPE: PRT
<213> ORGANISM: Human immunodeficiency virus

<400> SEQUENCE: 53

Leu Glu Ala Ile Pro Cys Ser Ile Pro Pro Glu Phe Leu Phe Gly Lys
1               5                   10                  15

Pro Phe Val Phe
            20

<210> SEQ ID NO 54
<211> LENGTH: 7
<212> TYPE: PRT
<213> ORGANISM: Human immunodeficiency virus

<400> SEQUENCE: 54

Gln Ile Trp Asn Asn Met Thr
1               5

<210> SEQ ID NO 55
<211> LENGTH: 10
<212> TYPE: PRT
<213> ORGANISM: Human immunodeficiency virus

<400> SEQUENCE: 55

Gly Ile Val Gln Gln Gln Asn Asn Leu Leu
1               5                   10
```